(12) United States Patent
Enan

(10) Patent No.: US 7,622,269 B2
(45) Date of Patent: *Nov. 24, 2009

(54) METHODS OF SCREENING TYRAMINE- AND OCTOPAMINE-EXPRESSING CELLS FOR COMPOUNDS AND COMPOSITIONS HAVING POTENTIAL INSECT CONTROL ACTIVITY

(75) Inventor: Essam Enan, Davis, CA (US)

(73) Assignee: Tyratech, Inc., Melbourne, FL (US)

( * ) Notice: Subject to any disclaimer, the term of this patent is extended or adjusted under 35 U.S.C. 154(b) by 472 days.

This patent is subject to a terminal disclaimer.

(21) Appl. No.: 11/086,615

(22) Filed: Mar. 21, 2005

(65) Prior Publication Data

US 2005/0214267 A1    Sep. 29, 2005

Related U.S. Application Data

(63) Continuation-in-part of application No. 10/832,022, filed on Apr. 26, 2004, now Pat. No. 7,541,155.

(60) Provisional application No. 60/554,968, filed on Mar. 19, 2004.

(51) Int. Cl.
  G01N 33/53    (2006.01)
  G01N 33/567   (2006.01)
  C12N 5/00     (2006.01)
  C12N 5/02     (2006.01)
  C07K 1/00     (2006.01)
  C07K 14/00    (2006.01)
  C07K 17/00    (2006.01)

(52) U.S. Cl. .................. 435/7.2; 435/325; 530/350

(58) Field of Classification Search .................. None
  See application file for complete search history.

(56) References Cited

U.S. PATENT DOCUMENTS

| | | | |
|---|---|---|---|
| 3,943,063 A | 3/1976 | Morishita et al. |
| 3,971,852 A | 7/1976 | Brenner et al. |
| 4,211,668 A | 7/1980 | Tate |
| 4,320,113 A | 3/1982 | Kydonieus |
| 4,434,181 A | 2/1984 | Marks et al. |
| 4,678,775 A | 7/1987 | Nathanson |
| 4,693,890 A | 9/1987 | Wilson et al. |
| 4,696,676 A | 9/1987 | Wilson et al. |
| 4,748,860 A | 6/1988 | Butler et al. |
| 4,759,228 A | 7/1988 | Butler et al. |
| 4,762,718 A | 8/1988 | Marks, Sr. |
| 4,764,367 A | 8/1988 | Wilson et al. |
| 4,783,457 A | 11/1988 | Nathanson |
| 4,801,446 A | 1/1989 | Wilson et al. |
| 4,801,448 A | 1/1989 | Wilson et al. |
| 4,808,403 A | 2/1989 | Wilson et al. |
| 4,816,248 A | 3/1989 | Wilson et al. |
| 4,818,526 A | 4/1989 | Wilson et al. |
| 4,859,463 A | 8/1989 | Wilson et al. |
| 4,876,087 A | 10/1989 | Wilson et al. |
| 4,880,625 A | 11/1989 | Wilson et al. |
| 4,885,855 A | 12/1989 | Marks et al. |
| 4,886,662 A | 12/1989 | Wilson et al. |
| 4,892,871 A | 1/1990 | Nathanson |
| 4,902,504 A | 2/1990 | Wilson et al. |
| 4,902,690 A | 2/1990 | Nathanson |
| 4,911,906 A | 3/1990 | Wilson et al. |
| 4,943,435 A | 7/1990 | Baker et al. |
| 4,959,209 A | 9/1990 | Wilson et al. |
| 4,970,068 A | 11/1990 | Wilson et al. |
| 4,988,507 A | 1/1991 | Wilson et al. |
| 4,988,508 A | 1/1991 | Wilson et al. |
| 4,988,509 A | 1/1991 | Wilson et al. |
| 4,990,684 A | 2/1991 | Hoelderich et al. |
| 4,992,270 A | 2/1991 | Wilson et al. |
| 5,091,423 A | 2/1992 | Wilson et al. |
| 5,118,711 A | 6/1992 | Wilson et al. |
| 5,126,369 A | 6/1992 | Wilson et al. |
| 5,134,892 A | 8/1992 | Wilson et al. |
| 5,165,926 A | 11/1992 | Wilson et al. |
| 5,175,175 A | 12/1992 | Wilson et al. |
| 5,196,200 A | 3/1993 | Wilson et al. |
| 5,204,372 A | 4/1993 | Wilson et al. |
| 5,205,065 A | 4/1993 | Wilson et al. |
| 5,228,233 A | 7/1993 | Butler et al. |
| 5,250,575 A | 10/1993 | Wilson et al. |
| 5,272,179 A | 12/1993 | Butler et al. |
| 5,281,621 A | 1/1994 | Wilson et al. |
| 5,321,048 A | 6/1994 | Wilson et al. |
| 5,327,675 A | 7/1994 | Butler et al. |
| 5,344,776 A | 9/1994 | Venter et al. |
| 5,344,847 A | 9/1994 | Wilson et al. |
| 5,354,783 A | 10/1994 | Marin et al. |
| 5,366,975 A | 11/1994 | Nathanson |
| 5,387,418 A | 2/1995 | Marin et al. |
| 5,401,500 A | 3/1995 | Warren et al. |

(Continued)

FOREIGN PATENT DOCUMENTS

WO    WO 98/54971    12/1998

(Continued)

OTHER PUBLICATIONS

Hiripi L, et al. Br. Res. 633 (1-2), 119-126, Jan. 7, 1994.*

(Continued)

*Primary Examiner*—Robert Landsman
(74) *Attorney, Agent, or Firm*—Davis Wright Tremaine LLP

(57) ABSTRACT

A screening method for identifying compounds that are effective insect control agents includes providing cells expressing an octopamine receptor, adding the compounds to the cells, and measuring the effects of the compounds and compositions. The effects of the compounds may be determined by measuring the binding affinity of the compounds to the octopamine receptor or measuring the change in intracellular cAMP or $Ca^{2+}$ levels.

18 Claims, 11 Drawing Sheets

U.S. PATENT DOCUMENTS

| | | | |
|---|---|---|---|
| 5,407,609 A | 4/1995 | Tice et al. |
| 5,409,958 A | 4/1995 | Butler et al. |
| 5,417,009 A | 5/1995 | Butler et al. |
| 5,418,010 A | 5/1995 | Janda et al. |
| 5,439,690 A | 8/1995 | Knight |
| 5,439,941 A | 8/1995 | Butler et al. |
| 5,441,988 A | 8/1995 | Butler et al. |
| 5,447,714 A | 9/1995 | Marin et al. |
| 5,449,695 A | 9/1995 | Marin et al. |
| 5,458,882 A | 10/1995 | Marin et al. |
| 5,464,626 A | 11/1995 | Warren et al. |
| 5,472,701 A | 12/1995 | Warren et al. |
| 5,474,898 A | 12/1995 | Venter et al. |
| 5,521,165 A | 5/1996 | Warren et al. |
| 5,576,010 A | 11/1996 | Warren et al. |
| 5,576,011 A | 11/1996 | Butler et al. |
| 5,593,600 A | 1/1997 | Solomon |
| 5,633,236 A | 5/1997 | Warren et al. |
| 5,635,173 A | 6/1997 | Warren et al. |
| 5,635,174 A | 6/1997 | Warren et al. |
| 5,665,781 A | 9/1997 | Warren et al. |
| 5,683,687 A | 11/1997 | Marin et al. |
| 5,693,344 A | 12/1997 | Knight et al. |
| 5,703,104 A | 12/1997 | Peck et al. |
| 5,753,686 A | 5/1998 | Marin et al. |
| 5,772,983 A * | 6/1998 | O'Connell et al. ............ 424/9.2 |
| 5,785,982 A | 7/1998 | Warren et al. |
| 5,814,325 A | 9/1998 | Rod |
| 5,840,669 A | 11/1998 | Neelakantan |
| 5,855,903 A | 1/1999 | Warren et al. |
| 5,980,931 A | 11/1999 | Fowler et al. |
| 5,990,178 A | 11/1999 | Ninkov |
| 5,998,484 A | 12/1999 | Zobitne et al. |
| 6,004,569 A | 12/1999 | Bessette et al. |
| 6,006,470 A | 12/1999 | Geoghegan et al. |
| 6,024,874 A | 2/2000 | Lott |
| 6,114,384 A | 9/2000 | Bessette et al. |
| 6,143,288 A | 11/2000 | Warren et al. |
| 6,183,767 B1 | 2/2001 | Bessette et al. |
| 6,255,356 B1 | 7/2001 | Butler |
| 6,272,790 B1 | 8/2001 | Paganessi et al. |
| 6,322,825 B1 | 11/2001 | Ninkov |
| 6,329,433 B1 | 12/2001 | Bessette et al. |
| 6,331,572 B1 | 12/2001 | Bessette et al. |
| 6,333,302 B1 | 12/2001 | Beer et al. |
| 6,333,360 B1 | 12/2001 | Bessette et al. |
| 6,340,710 B1 | 1/2002 | Bessette et al. |
| 6,342,535 B1 | 1/2002 | Bessette et al. |
| 6,342,536 B1 | 1/2002 | Bessette et al. |
| 6,360,477 B1 | 3/2002 | Flashinski et al. |
| 6,368,508 B1 | 4/2002 | Gatz et al. |
| 6,372,801 B1 | 4/2002 | Bessette et al. |
| 6,372,803 B1 | 4/2002 | Bessette et al. |
| 6,376,556 B1 | 4/2002 | Bessette et al. |
| 6,395,789 B1 | 5/2002 | Bessette et al. |
| 6,414,036 B1 | 7/2002 | Ninkov |
| 6,451,844 B1 | 9/2002 | Watkins et al. |
| 6,506,707 B1 | 1/2003 | Bessette |
| 6,531,163 B1 | 3/2003 | Bessette et al. |
| 6,534,099 B1 | 3/2003 | Bessette et al. |
| 6,548,085 B1 | 4/2003 | Zobitne et al. |
| 6,555,121 B1 | 4/2003 | Bessette et al. |
| 6,610,254 B1 | 8/2003 | Furner et al. |
| 6,649,660 B2 | 11/2003 | Ninkov |
| 6,660,288 B1 | 12/2003 | Behan et al. |
| 6,670,311 B1 | 12/2003 | Aldcroft et al. |
| 6,689,395 B2 | 2/2004 | Bessette |
| 6,713,518 B1 | 3/2004 | Bessette et al. |
| 6,812,258 B2 | 11/2004 | Bessette et al. |
| 6,841,577 B2 | 1/2005 | Bessette et al. |
| 6,844,369 B2 | 1/2005 | Ninkov |
| 6,849,614 B1 | 2/2005 | Bessette et al. |
| 6,858,653 B1 | 2/2005 | Bessette |
| 6,887,899 B1 | 5/2005 | Bessette |
| 6,921,539 B2 | 7/2005 | Ninkov |
| 6,949,587 B1 | 9/2005 | Bessette |
| 6,969,522 B2 | 11/2005 | Bessette |
| 6,974,584 B2 | 12/2005 | Bessette |
| 6,986,898 B1 | 1/2006 | Bessette |
| 7,008,649 B2 | 3/2006 | Bessette et al. |
| 7,109,240 B2 | 9/2006 | Bessette et al. |
| 7,201,926 B2 | 4/2007 | Fried et al. |
| 7,208,519 B2 | 4/2007 | Ninkov |
| 7,238,726 B2 | 7/2007 | Bessette |
| 7,238,798 B2 | 7/2007 | Lee et al. |
| 7,241,806 B2 | 7/2007 | Bessette |
| 7,250,175 B2 | 7/2007 | Bessette et al. |
| 7,291,650 B2 | 11/2007 | Bessette et al. |
| 7,320,966 B2 | 1/2008 | Bessette et al. |
| 7,351,420 B2 | 4/2008 | Bessette et al. |
| 7,357,939 B2 | 4/2008 | Bessette |
| 7,361,366 B2 | 4/2008 | Bessette et al. |
| 7,381,431 B2 | 6/2008 | Baker et al. |
| 2002/0028256 A1 | 3/2002 | Bessette |
| 2002/0034556 A1 | 3/2002 | Khazan |
| 2002/0073928 A1 | 6/2002 | Ingman et al. |
| 2002/0076360 A1 | 6/2002 | Ingman et al. |
| 2002/0081230 A1 | 6/2002 | Ingman et al. |
| 2002/0096121 A1 | 7/2002 | Ingman et al. |
| 2002/0107287 A1 | 8/2002 | Bessette et al. |
| 2003/0026823 A1 | 2/2003 | Fried et al. |
| 2003/0036530 A1 | 2/2003 | Bessette |
| 2003/0039674 A1 | 2/2003 | Bessette |
| 2003/0091657 A1 | 5/2003 | Chiasson |
| 2003/0091661 A1 | 5/2003 | Bessette |
| 2003/0108622 A1 | 6/2003 | Bessette et al. |
| 2003/0108623 A1 | 6/2003 | Bessette et al. |
| 2003/0175369 A1 | 9/2003 | Khazan-Enache |
| 2003/0194454 A1 | 10/2003 | Bessette et al. |
| 2004/0146595 A1 | 7/2004 | Bessette et al. |
| 2004/0156922 A1 | 8/2004 | Bessette et al. |
| 2004/0185080 A1 | 9/2004 | Hojo et al. |
| 2004/0192551 A1 | 9/2004 | Bessette |
| 2004/0213822 A1 | 10/2004 | Birch et al. |
| 2004/0248791 A1 | 12/2004 | Spana et al. |
| 2005/0004233 A1 | 1/2005 | Bessette et al. |
| 2005/0008714 A1 | 1/2005 | Enan |
| 2005/0013885 A1 | 1/2005 | Chiasson |
| 2005/0019269 A1 | 1/2005 | Marks et al. |
| 2005/0070576 A1 | 3/2005 | Spooner-Hart et al. |
| 2005/0136089 A1 | 6/2005 | Bessette et al. |
| 2005/0143260 A1 | 6/2005 | Bessette et al. |
| 2005/0147636 A1 | 7/2005 | Bessette et al. |
| 2005/0163869 A1 | 7/2005 | Bessette et al. |
| 2005/0170024 A1 | 8/2005 | Bessette et al. |
| 2005/0170025 A1 | 8/2005 | Bessette et al. |
| 2005/0170026 A1 | 8/2005 | Bessette et al. |
| 2005/0260241 A1 | 11/2005 | Bessette et al. |
| 2005/0260242 A1 | 11/2005 | Bessette et al. |
| 2005/0288227 A1 | 12/2005 | Marks et al. |
| 2006/0088564 A1 | 4/2006 | Bessette |
| 2006/0115507 A1 | 6/2006 | Bessette |
| 2006/0115508 A1 | 6/2006 | Bessette |
| 2006/0115509 A1 | 6/2006 | Bessette |
| 2006/0115510 A1 | 6/2006 | Bessette |
| 2006/0121074 A1 | 6/2006 | Bessette |
| 2007/0098750 A1 | 5/2007 | Bessette |
| 2007/0178128 A1 | 8/2007 | Bessette |
| 2007/0190094 A1 | 8/2007 | Bessette |
| 2007/0207221 A1 | 9/2007 | Bessette et al. |
| 2007/0298131 A1 | 12/2007 | Bessette et al. |
| 2007/0299037 A1 | 12/2007 | Bessette et al. |
| 2007/0299038 A1 | 12/2007 | Bessette et al. |
| 2008/0003315 A1 | 1/2008 | Bessette et al. |

| | | | |
|---|---|---|---|
| 2008/0003316 | A1 | 1/2008 | Bessette et al. |
| 2008/0003317 | A1 | 1/2008 | Bessette et al. |
| 2008/0004240 | A1 | 1/2008 | Bessette et al. |
| 2008/0015167 | A1 | 1/2008 | Bessette et al. |
| 2008/0015249 | A1 | 1/2008 | Bessette et al. |
| 2008/0020381 | A1 | 1/2008 | Henrich et al. |
| 2008/0032387 | A1 | 2/2008 | Bailey et al. |
| 2008/0038383 | A1 | 2/2008 | Bessette et al. |
| 2008/0153904 | A1 | 6/2008 | Bessette et al. |

FOREIGN PATENT DOCUMENTS

| | | |
|---|---|---|
| WO | WO 99/21891 | 5/1999 |
| WO | WO 99/33973 | 7/1999 |
| WO | WO 00/05964 | 2/2000 |
| WO | WO 00/21364 | 4/2000 |
| WO | WO 00/50566 | 8/2000 |
| WO | WO 00/51436 | 9/2000 |
| WO | WO 00/53020 | 9/2000 |
| WO | WO 00/75322 | 12/2000 |
| WO | WO 01/00020 | 1/2001 |
| WO | WO 01/00026 | 1/2001 |
| WO | WO 01/00032 | 1/2001 |
| WO | WO 01/00033 | 1/2001 |
| WO | WO 01/00034 | 1/2001 |
| WO | WO 01/00049 | 1/2001 |
| WO | WO 01/10214 | 2/2001 |
| WO | WO 01/18201 | 3/2001 |
| WO | WO 01/60163 | 8/2001 |
| WO | WO 01/91554 | 12/2001 |
| WO | WO 01/91556 | 12/2001 |
| WO | WO 01/91560 | 12/2001 |
| WO | WO 03/016477 | 2/2003 |
| WO | WO 2004/006968 | 1/2004 |
| WO | WO 2004/100971 | 11/2004 |
| WO | WO 2005/092016 | 10/2005 |

OTHER PUBLICATIONS

Reale V, et al. Br. Res. 769(2), 309-320, Sep. 26, 1997.*
Griffin G, et al. Eur. J. Pharmacol. 377:117-125, 1999.*
Bischof, et al.; *Cloning, expression and functional analysis of an octopamine receptor from Periplaneta Americana*; Insect Biochem Mol Biol; 34:6:511-521, Jun. 2004.
Chirgwin et al., 18 *Biochemistry* 5294-5299 (1979).
Coats, et al.; *Toxicity and neurotoxic effects of monoterpenoids in insects and earthworms*; ACS publication; 1991.
Enan, Essam, et al.; *Insecticidal action of terpenes and phenols to cockroaches: effect on octopamine recetors*; International Symposium on Crop Protection, Ghent, Belgium; May 1998.
Enan, Essam; *Insecticidal activity of essential oils: octopaminergic sites of action*; Comp. Biochem. Physiol. C Toxicol.; 130:325-337; 2001.
Evans, et al.; *Agonist-specific coupling of G-protein-coupled receptors to second-messenger systems*; Progress in Brain Research; vol. 106; 1999; 259-268.
Gudermann, et al., "Functional and structural complexity of signal transduction via G-protein-coupled receptors," *Annu Rev Neurosci* 20:399-427; 1997.
Kutsukake, Mayako, et al; *A tyramine receptor gene mutation causes a defective olfactory behavior in Drosophila*; Gene; Mar. 7, 2000; 245:1, 31-42.
Kyte et al., J. Mol. Biol. 157, 105-132 (1982).
Muller-Riebau, et al.; *Chemical Composition and Fungitoxic Properties to Phytopathogenic Fungi of Essential Oils of Selected Aromatic Plant Growing Wild in Turkey*; J Agric. Food chem.; 43: 2262-2266; 1995.
Rice, et al.; *Insecticidal properties of monoterpenoid derivatives to the house fly (diptera: muscidae) and red flour beetle (coleoptera: tenebrionidae)*; Pesticide Science; vol. 44; 1994; 195-202.
Rice, et al.; *Bioregulators for Crop Protection and Pest Control*, Chapter Structural requirements for Monoterpenoid Activity Against Insects; American Chemical Society Symposium Series developed from a symposium sponsored by the Division of Agrochemicals at the 205th National Meeting of the American Chemical Society in Denver, Colorado, Mar. 28-Apr. 2, 1993.
Robb, S., et al.; *Agonist-specific coupling of a cloned Drosophila octopamine/tyramine receptor to multiple second messenger systems*; EMBO J.; Mar. 15, 1994; 13:6; 1325-1330.
Saudou, F., et al.; *Cloning and characterization of a Drosophila tyramine receptor*; EMBO J.; Nov. 1990; 9:11; 3611-3617.
Tsao, et al.: *Monoterpenoids and their synthetic derivatives as leads for new insect-control agents*; American Chemical Society; Chapter 28; 1995.
Von Nickisch-Rosenegk, et al.; *Cloning of biogenic amine receptors from moths (Bombyx mori and Heliothis virescens)*; Insect Biochem Mol Biol; Sep.-Oct. 1996; 26:8-9; 817-827.
Abou El Ela, et al. 2001. "Insecticidal activity of some essential oils: cAMP mediates effects." *Bulletin of High Institute of Public Health* 31(1):15-30, 2001.
Alvarez-Sanchez, et al., 2000. "A novel cysteine proteinase (CP65) of *Trichomonas vaginalis* involved in cytotoxicity."*Microb Pathog.* 28(4):193-202.
Aoyama, et al., 2001. "Substituent-dependent, positive and negative modulation of *Bombyx mori* adenylate cyclase by synthetic octopamine/tyramine analogues." *Arch Insect Biochem Physiol.* 47(1):1-7.
Arakawa, et al. 1990. "Cloning, localization, and permanent expression of a Drosophila octopamine receptor." *Neuron.* 4(3):343-354.
Baxter, et al. 1999. "Isolation of a cDNA for an octopamine-like, G-protein coupled receptor from the cattle tick, *Boophilus microplus*." *Insect Biochem Mol Biol.* 29(5):461-467.
Berntzen, et al. 1965. "In vitro hatching of oncosphere of Hymenolepidid cestodes." *J Parasitol.* 51(2):235-242.
Blenau, et al. 2000. "Amtyrl: characterization of a gene from honeybee (*Apis mellifera*) brain encoding a functional tyramine receptor." *J Neurochem.* 74(3):900-908.
Blenau, et al. 2001. "Molecular and pharmacological properties of insect biogenic amine receptors: lessons from *Drosophila melanogaster* and *Apis mellifera*." *Arch Insect Biochem Physiol.* 48(1):13-38.
Borowsky, et al. 2001. "Trace amines: Identification of a family of mammalian G protein-coupled receptors." *Proc Natl Acad Sci USA.* 98(16):8966-8971.
Bunzow, et al. 2001. "Amphetamine, 3,4-Methylenedioxymethamphetamine, Lysergic Acid Diethylamide, and Metabolites of the Catecholamine Neurotransmitters Are Agonists of a Rat Trace Amine Receptor." *Mol Pharmacol* 60(6):1181-1188.
Coats, Joel R. 1990. "Mechanisms of toxic action and structure-activity relationships for organochlorine and synthetic pyrethroid insecticides." *Environ Health Prespect.* 87:255-262.
Colby, S.R. 1967. "Calculating synergistic and antagonistic responses of herbicide combinations." *Weeds.* 15(1):20-22.
Cooley, et al. 1988. "Insertional mutagenesis of the Drosophila genome with single P elements" *Science.* 239(4844):1121-1128.
Donini, et al. 2004. "Evidence for a possible neurotransmitter/neuromodulator role of tyramine on the locust oviducts." *J Insect Physiol.* 50(4):351-361.
Downer, et al. 1993. "Characterization of the tyraminergic system in the central nervous system of the locust, *Locusta migratoria migratoides*." *Neurochem Res.* 18(12):1245-1248.
Downer, et al. 1994. "Biogenic amines in insects." *Insect Neurochemistry and Neurophysiology* 1993 23-38.
Dudai, et al. 1982. "Aminergic receptors in *Drosophila melanogaster*: properties of [3H]dihydroergocryptine binding sites." *J Neurochem.* 38(6):1551-1558.
Enan, et al. 1996. "Deltamethrin induced thymus atrophy in male Balb/c mice." *Biochem Pharmacol.* 51(4):447-454.
Evans, et al. 1980. "Action of formamidine pesticides on octopamine receptors." *Nature* 287(5777):60-62.
Evans, PD 1981. "Multiple receptor types for octopamine in the locust." *J Physiol.* 318:99-122.
Evans, et al. 1995. "Agonist-specific coupling of G-protein-coupled receptors to second-messenger systems." *Prog Brain Res.* 106:259-268.

Finney, D.J. 1971. "Probit Analysis." *Cambridge at the University Press* 33-37.

Gerhardt, et al. 1997. "Molecular cloning and pharmacological characterization of a molluscan octopamine receptor." *Mol Pharmacol.* 51(2):293-300.

Grodnitzky, et al. 2002. "QSAR evaluation of monoterpenoids' insecticidal activity." *J Agric Food Chem.* 50(16):4576-4580.

Grundy, et al. 1985. "Inhibition of acetylcholinesterases by pulegone-1,2-epoxide." *Pestic Biochem Physiol.* 23(3):383-388.

Gudermann, et al. 1996. "Diversity and selectivity of receptor-G protein interaction." *Annu Rev Pharmacol Toxicol.* 36:429-459.

Guillen, et al. 1989. "A possible new class of octopamine receptors coupled to adenylate cyclase in the brain of the dipterous Ceratitis capitata. Pharmacological characterization and regulation of 3H-octopamine binding." *Life Sci.* 45(7):655-662.

Han, et al. 1998. "A novel octopamine receptor with preferential expression in Drosophila mushroom bodies." *J Jeurosci.* 18(10):3650-3658.

Hori, Masatoshi 1999. "The effects of rosemary and ginger oils on the alighting behavior of *Myzus persicae* (Sulzer) (Homoptera: Aphididae) and on the incidence of yellow spotted streak." *Appl Entomol Zool.* 34(3):351-358.

International Search Report and the Written Opinion of the International Searching Authority for in International Application No. PCT/US2004/012947, dated Nov. 5, 2004, 6 pages.

Ito, Akira 1975. "In vitro oncospheral agglutination given by immune sera from mice infected and rabbits injected with eggs of *Hymenolepis nana.*" *Parasitology.* 71(3):465-473.

Karr, et al. 1992. "Effects of four monoterpenoids on growth and reproduction of the German cockroach (Blattodea: Blattellidae)." *J Econ Entomol.* 85(2),424-429.

Khan, et al. 2003. "Positive and negative modulation of *Bombyx mori* adenylate cyclase by 5-phenyloxazoles: identification of octopamine and tyramine receptor agonists." *Arch Insect Biochem Physiol.* 52(1):7-16.

Kostyukovsky, et al. 2002. "Activation of octopaminergic receptors by essential oil constituents isolated from aromatic plants: possible mode of action against insect pests." *Pest Manag Sci.* 58(11):1101-1106.

Kravitz, et al. 1976. "Octopamine neurons in lobsters." *Neurosci Symp.* 1:67-81.

Krymskaya, et al. 2000. "Mechanisms of Proliferation Synergy by Receptor Tyrosine Kinase and G Protein-Coupled Receptor Activation in Human Airway Smooth Muscle." *Am J Respir Cell Mol Biol.* 23(4):546-554.

Landolt, et al. 1999. "Plant Essential Oils as Arrestants and Repellents for Neonate Larvae of the Codling Moth (Lepidoptera: Tortricidae)." *Environ Entomol.* 28(6):954-960.

Lee S, et al. 1997. "Insecticidal activity of monoterpenoids to western corn rootworm (Coleoptera: Chrysomelidae), twospotted spider mite (Acari: Tetranychidae), and house fly (Diptera: Muscidae)." *J Econ Entomol.* 90(4):883-892.

Lomasney, et al. 1990. "Expansion of the alpha 2-adrenergic receptor family: cloning and characterization of a human alpha 2-adrenergic receptor subtype, the gene for which is located on chromosome 2." *Proc Natl Acad Sci USA.* 87(13):5094-5098.

Lynn, Dwight E. 1996. "Development and characterization of insect cell lines." *Cytotechnology* 20(2):3-11.

Lynn, Dwight E. 2002. "Methods for Maintaining Insect Cell Cultures." *J Insect Sci.* 1-6.

Menevse, et al. 1977. "Evidence for the specific involvement of cyclic AMP in the olfactory transduction mechanism." *Biochem Biophys Res Com.* 77(2):671-677.

Michon, et al. 2002. "Evolutionary relationships of conserved cysteine-rich motifs in adhesive molecules of malaria parasites." *Mol Biol Evol.* 19(7):1128-1142.

Miyazawa, et al. 1997. "Inhibition of Acetylcholinesterase Activity by Monoterpenoids with a p-Menthane Skeleton." *J Agric Food Chem.* 45(3):677-679.

Morty, et al. 1999. "Oligopeptidase B from *Trypanosoma brucei*, a new member of an emerging subgroup of serine oligopeptidases." *J Biol Chem.* 274(37):26149-26156.

Ngoh, et al.1998. "Insecticidal and repellent properties of nine volatile constituents of essential oils against the American cockroach, *Periplaneta americana* (L.)." *Pestic Sci.* 54(3):261-268.

Nok, et al. 2003. "Characterization of sialidase from Entamoaeba hystolitica and possible pathogenic role in amebiasis." *Parasitol Res.* 89(4):302-307.

Office Action for U.S. Appl. No. 10/832,022, filed Apr. 26, 2004, dated May 17, 2007, 7 pages.

Office Action for U.S. Appl. No. 10/832,022, filed Apr. 26, 2004, dated Jan. 25, 2008, 6 pages.

Office Action for U.S. Appl. No. 10/832,022, filed Apr. 26, 2004, dated Oct. 10, 2008, 5 pages.

Office Action for U.S. Appl. No. 11/870,385, filed Oct. 10, 2007, dated Oct. 8, 2008, 9 pages.

Office Action for U.S. Appl. No. 11/365,426, filed Mar. 1, 2006, dated Aug. 28, 2008, 14 pages.

Office Action for U.S. Appl. No. 11/365,426, filed Mar. 1, 2006, dated Mar. 24, 2009, 5 pages.

Ohta, et al. 2003. "B96Bom encodes a *Bombyx mori* tyramine receptor negatively coupled to adenylate cyclase." *Insect Mol Biol.* 12(3):217-223.

Orchard, Ian 1982. "Octopamine in insects: neurotransmitter, neurohormone, and neuromodulator." *Can J Zool.* 60:659-669.

Pearson, et al. 1983. "Praziquantel: a major advance in anthelminthic therapy." *Ann Intern Med.* 99(2):195-198.

Rex, et al. 2002. "Characterization of a tyramine receptor from *Caenorhabditis elegans.*" *J Neurochem.* 82(6):1352 1359.

Robertson, et al. 1976. "Octopamine and some related noncatecholic amines in invertebrate nervous systems." *Int Rev Neurobiol.* 19:173-224.

Roeder, Thomas 1992. "A new octopamine receptor class in locust nervous tissue, the octopamine 3 (OA3) receptor." *Life Sci.* 50(1):21-28.

Roeder, T. 1994. "Biogenic amines and their receptors in insects." *Comp Biochem Physiol.* 107C(1):1-12.

Roeder, T. 1999. "Octopamine in invertebrates." *Prog Neurobiol.* 59(5):533-561.

Ryan, et al. 1988. "Plant-insect coevolution and inhibition of acetylcholinesterase." *J Chem Eco.* 14(10):1965-1975.

Sangwan, et al. 1990. "Nematicidal activity of some essential plant oils." *Pestic Sci.* 28(3):331-335.

Sawamura, et al. 1999. "Inhibitory Effects of Citrus Essential Oils and Their Components on the Formation of N-Nitrosodimethylamine." *J Agric Food Chem.* 47(12):4868-4872.

Shulaev, et al. 1997. "Airborne signalling by methyl salicylate in plant pathogen resistance." *Nature* 385(6618):718-721.

Urban, et al. 1999. "An ATP-driven efflux pump is a novel pathogenicity factor in rice blast disease." *EMBO J.* 18(3):512-521.

Van Poyer, et al. 2001. "Phenolamine-dependent adenylyl cyclase activation in Drosophila Schneider 2 cells." *Insec Biochem Mol Biol.* 31:333-338.

Vanden Broeck, et al. 1995. "Characterization of a cloned locust tyramine receptor cDNA by functional expression in permanently transformed Drosophila S2 cells." *J Neurochem.* 64(6):2387-2395.

Vernier, et al. 1995. "An evolutionary view of drug-receptor interaction: the bioamine receptor family." *Trends Pharmacol Sci.* 16(11):375-385.

Yu, et al. 2002. "A common oocyst surface antigen of Cryptosporidium recognized by monoclonal antibodies." *Parasitol Res.* 88(5):412-420.

* cited by examiner

```
                                                          TM 1                                                          TM 2
MRDGVMNASTCSALLEQVAWDDEGLIASLVVLLLINVMVIVGNCLVIAAVFMSSKLRSVTNLFIVSRAVADLMVGLAVLPFSATW
MNE-----TECEDLIKSVKWTEPANLISLAVLEFINVLVIGGNCLVIAAVFCSNKLRSVTNFFIVNLAVADLLVGLAVLPFSATW
                              TM 3                                                  TM 4
EVFKVWIFGDVWCSIWLAVDVWMCTASIINLCAISLDRYVAVTRPVTYPSIMSSGRAKLIIAGVWVLSFVICFPPLVGWKDKRE-
EVFKVWIFGDLMCRIWLAVDVWMCTASIINLCAISLDRYVAVTRPVTYPSIMSTKKAKSLIAGIWVLSFFICFPPLVGWKDQKAV

-DPP-SNSSGSLF-----------------GSRPLTPPA--------------------------------------------
IQPTYPKGNHTLYYITTMSSSEDQLGLDSIKDQGEASLPPSPPHIGNGNAYNPYDPGFAPIDGSAEIRLAAIDSTSTSTTATTT
                                                     TM 5
------------LQ--------VPAPCPWICELTNDAGYVVVYSALGSEYLPMLVMLFFYWRIYRAAVQTTRAINQGFRT
TTASSSSTTETEMDLDLINAPPQNRPQTISGSCPWKCELTNDRGYVLYSALGSEYIPMFVMLFFYWRIYRAAVRTTRAINQGFKT

TKGS-RTIGN-RFDEQRITLRIHRGRGSSVMRHGPTPPPSSSSQQDSSVTETSLASSVCGSPSSGATSSSAVKSPECQRLTRSST-
TKGSPRESGNNRVDESQILRIHRGRPCSTPQRTPLSVHSMSSTLSVNSNGGGGAV--ASGLGASTEDHLQGGAPKRATSMRVC

RRSNKPIKISVSYPSSDAICMAGSNNGGVPSSSPSPNSSKKSSFSSSSPPPGLYSVHYSNGGREAT--SSVYRSRDPNCHLRVTG
RQRHEKVAIKVSFPSSEM----LDAGQPQASPH--------------------------YAVISSANGRRASFKTSLFDIGETTNLDAAA

SRLASHNRRGSSVRRRSSIDSTITPGAAQQLLEDKDLSPSPTEDDSGSAKPKLISRMGKRNIKAQVKREMETKAAKTLGIIVGG
S---------------GPGDIETGLSTTSLSAK--------------------KRAGKRSAKFQVKREMETKAAKTIAIIVGG
                    TM 6                                              TM 7
FIVCWLPFFTMYLVRAFCEDCIHHLLFSVLFWIGYCNSAINPCIYALFSKDFREAFKRIICRCFCARKIKKETRDWARRRGSDGS
FIVCWLPFFTMYLIRAFQDHCIQPTVFSVLFWIGYCNSAINPMIYALFSNEFRIAFKRIVCRCVCTR-------SGFRASENF

QLGARGPEPGSERGRSPSNNNTQQYPHNSVGEDSDQGNDGSDSR    P. americana Pa oa1 (628 amino acids)
QMIA--------ARALMAPATF-HKTISGCSDDG-EGVDFS       D. melanogaster OAMB (637 amino acids)
```

FIGURE 2

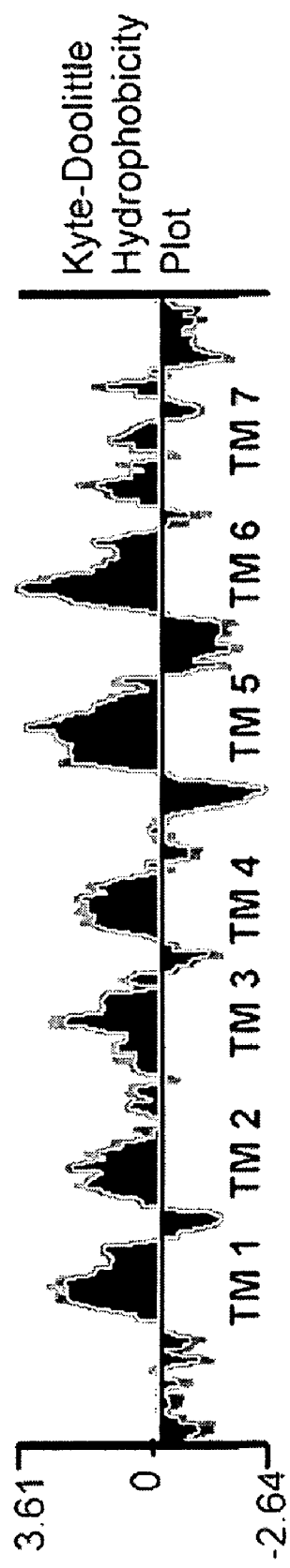
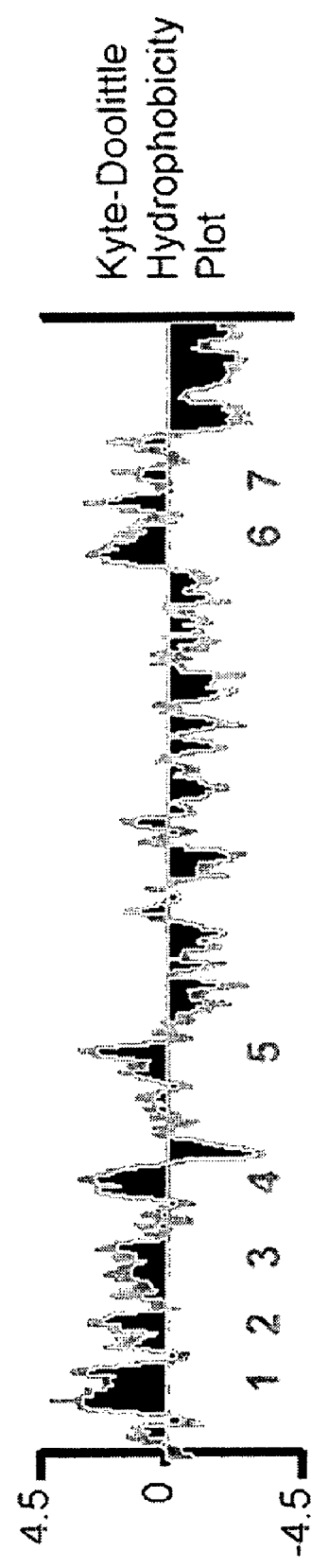
Figure 4

SEQUENCE LISTING

<160> NUMBER OF SEQ ID NOS: 13

<210> SEQ ID NO 1
<211> LENGTH: 2330
<212> TYPE: DNA
<213> ORGANISM: Periplaneta americana

<400> SEQUENCE: 1

```
agagaagttg aactgggttt cttcaaaata aacagtaaaa aattgagtct gaagaattcc      60
atatcgtgac tggtgctggc acggcaatat ggcgagtgag tgaccctgat gagggacggg     120
gttatgaacg ctagcacttg ctccgctctg ctggagcagg tcgcctggga tgaccctggt     180
ctgatcgcct ccctcgtcgt gctcctgctc atcaacgtca tggtcatcgt cggcaactgc     240
ctcgtcatcg ctgccgtctt catgagctcg aagctgcgtt ccgtaaccaa cctgttcata     300
gtgtcgctgg ccgtcgctga tctcatggtg ggactcgccg ttctcccgtt cagcgccacc     360
tgggaggtat tcaaggtgtg gatcttcgga gacgtgtggt gctccatctg gttggcggtg     420
gacgtgtgga tgtgcacggc ctccatcttg aacctgtgtg ccatctcctt ggaccgctac     480
gtggccgtca cgcgtcccgt cacgtatcct agcatcatgt cgtcggggcg tgccaaattg     540
ctcattgcag gagtgtgggt cctgagcttc gtgatctgct tcccgccgct ggtcggctgg     600
aaagacaaac gagaggaccc tcccagcaac agcagcggat ctctctttgg gtctcggccc     660
ctcaccccac cgccggcact acaggttccg gctccgtgcc cctggatctg tgagctgacg     720
aacgacgcgg gctatgtggt gtactccgcg ctagggtcct tctacctccc catgctagtg     780
atgttgttct tctactggcg catataccgc gccgcagtgc agaccacacg cgccatcaac     840
cagggcttcc gcaccaccaa gggctcgcgt accatcggca accgcttcga cgagcaacgt     900
ctcactctgc gcatacacag ggggcgggc tcctcggtga tgcggcacgg gccgacgccg     960
ccgccgtcgt cctcgcagca agacagcagt gtcacagaga cgagcctggc cagcagtgcg    1020
tgcgggtcgc cgagcagcgg cgcgacgtcc tcgagcgccg tcaagtcgcc cgagtgccag    1080
cgcctcacgc gctcctccac cagacgcagc aacaagccca tcaagatcag cgtgagctac    1140
cccagcagcg acgccatctg catggccggc agcaacaacg gtggggtgcc ctcctcatcg    1200
cccagtccca acagctccaa gaagtccagc ttctcttctt cctccctcc cccaggactc    1260 tattctgttc actattccaa tggcggccgc gaggctacct cgtccgtgta ccgcagtcga    1320
gatccgaact gccacctccg ggtgacggga tctcgcctgg cgtctcacaa ccgccgaggc    1380
agcagcgtcc gacgccgcag cagtactgac agcacgctga cgcctggcgc tgcgcagcag    1440
ttgctggaag acaaggatct gtccccgtca ccgactttcg acgacagcgg gtcggcgaag    1500
cccaagctga tctccaggat gggaaaacgc aacatcaaag cgcaggtcaa gcgctttcgg    1560
atggagacca aggcggccaa gacgcttggc attatagtag gcggcttcat cgtgtgctgg    1620
```

-continued

```
ctaccgttct tcaccatgta cctggttaga gcattctgtg aggattgcat ccaccacctt    1680
ctcttctccg tcctcttctg gctgggctat tgcaactctg ccatcaatcc ctgcatatac    1740
gccctcttta gcaaggactt ccgattcgct ttcaagagga tcatctgcag gtgttttgc     1800 gcgaggaaga tcaagaagga gacgagagac tgggctcgaa gacggggctc cgacggctcc    1860
cagctcggag cacgaggccc tgaacccggt tcggaaagag ggaggtcgcc ctccaacaac    1920
aacactcagc agtatcctca caactcggta ggagaggaca gcgaccaagg caacgatgga    1980
tcggactcca ggtgacctcc actaatgcca ctcacagcgt agggcagggt tcgttgcctg    2040
agagaccaga gagtcctccg caacattgtc ctgtgcagct gaaatgggtt cggaccttcc    2100
acgagcaggt gtcctccaga ctcgtgcctg cagcggtctg gagggtcact tggagtgatg    2160
caggtctgag agttggcatg cttcggtctt caagaacaac cggaaagttg ttgcatcgat    2220
ttatgcttta tctttgaagc tgaaaggttc gaagtgtcct agtgaatgca caggcttgcc    2280
aaaatattga atcagttgaa atgcaaaaaa aaaaaaaaaa aaaaaaaaa                 2330
```

<210> SEQ ID NO 2
<211> LENGTH: 628
<212> TYPE: PRT
<213> ORGANISM: Periplaneta americana

<400> SEQUENCE: 2

```
Met Arg Asp Gly Val Met Asn Ala Ser Thr Cys Ser Ala Leu Leu Glu
1               5                   10                  15

Gln Val Ala Trp Asp Asp Pro Gly Leu Ile Ala Ser Leu Val Val Leu
            20                  25                  30

Leu Leu Ile Asn Val Met Val Ile Val Gly Asn Cys Leu Val Ile Ala
        35                  40                  45

Ala Val Phe Met Ser Ser Lys Leu Arg Ser Val Thr Asn Leu Phe Ile
    50                  55                  60

Val Ser Leu Ala Val Ala Asp Leu Met Val Gly Leu Ala Val Leu Pro
65                  70                  75                  80

Phe Ser Ala Thr Trp Glu Val Phe Lys Val Trp Ile Phe Gly Asp Val
                85                  90                  95

Trp Cys Ser Ile Trp Leu Ala Val Asp Val Trp Met Cys Thr Ala Ser
            100                 105                 110

Ile Leu Asn Leu Cys Ala Ile Ser Leu Asp Arg Tyr Val Ala Val Thr
        115                 120                 125

Arg Pro Val Thr Tyr Pro Ser Ile Met Ser Ser Gly Arg Ala Lys Leu
    130                 135                 140

Leu Ile Ala Gly Val Trp Val Leu Ser Phe Val Ile Cys Phe Pro Pro
145                 150                 155                 160

Leu Val Gly Trp Lys Asp Lys Arg Glu Asp Pro Pro Ser Asn Ser Ser
                165                 170                 175

Gly Ser Leu Phe Gly Ser Arg Pro Leu Thr Pro Pro Ala Leu Gln
            180                 185                 190

Val Pro Ala Pro Cys Pro Trp Ile Cys Glu Leu Thr Asn Asp Ala Gly
        195                 200                 205

Tyr Val Val Tyr Ser Ala Leu Gly Ser Phe Tyr Leu Pro Met Leu Val
    210                 215                 220

Met Leu Phe Phe Tyr Trp Arg Ile Tyr Arg Ala Ala Val Gln Thr Thr
225                 230                 235                 240

Arg Ala Ile Asn Gln Gly Phe Arg Thr Thr Lys Gly Ser Arg Thr Ile
```

-continued

```
                245                 250                 255
Gly Asn Arg Phe Asp Glu Gln Arg Leu Thr Leu Arg Ile His Arg Gly
            260                 265                 270

Arg Gly Ser Ser Val Met Arg His Gly Pro Thr Pro Pro Ser Ser
        275                 280                 285

Ser Gln Gln Asp Ser Ser Val Thr Glu Thr Ser Leu Ala Ser Ser Ala
        290                 295                 300

Cys Gly Ser Pro Ser Ser Gly Ala Thr Ser Ser Ala Val Lys Ser
305                 310                 315                 320

Pro Glu Cys Gln Arg Leu Thr Arg Ser Ser Thr Arg Arg Ser Asn Lys
                325                 330                 335

Pro Ile Lys Ile Ser Val Ser Tyr Pro Ser Ser Asp Ala Ile Cys Met
            340                 345                 350

Ala Gly Ser Asn Asn Gly Gly Val Pro Ser Ser Pro Ser Pro Asn
        355                 360                 365

Ser Ser Lys Lys Ser Ser Phe Ser Ser Ser Pro Pro Gly Leu
        370                 375                 380

Tyr Ser Val His Tyr Ser Asn Gly Gly Arg Glu Ala Thr Ser Ser Val
385                 390                 395                 400

Tyr Arg Ser Arg Asp Pro Asn Cys His Leu Arg Val Thr Gly Ser Arg
                405                 410                 415

Leu Ala Ser His Asn Arg Arg Gly Ser Ser Val Arg Arg Ser Ser
                420                 425                 430

Thr Asp Ser Thr Leu Thr Pro Gly Ala Ala Gln Gln Leu Leu Glu Asp
        435                 440                 445

Lys Asp Leu Ser Pro Ser Pro Thr Phe Asp Asp Ser Gly Ser Ala Lys
450                 455                 460

Pro Lys Leu Ile Ser Arg Met Gly Lys Arg Asn Ile Lys Ala Gln Val
465                 470                 475                 480

Lys Arg Phe Arg Met Glu Thr Lys Ala Ala Lys Thr Leu Gly Ile Ile
                485                 490                 495

Val Gly Gly Phe Ile Val Cys Trp Leu Pro Phe Phe Thr Met Tyr Leu
            500                 505                 510

Val Arg Ala Phe Cys Glu Asp Cys Ile His His Leu Leu Phe Ser Val
        515                 520                 525

Leu Phe Trp Leu Gly Tyr Cys Asn Ser Ala Ile Asn Pro Cys Ile Tyr
        530                 535                 540

Ala Leu Phe Ser Lys Asp Phe Arg Phe Ala Phe Lys Arg Ile Ile Cys
545                 550                 555                 560

Arg Cys Phe Cys Ala Arg Lys Ile Lys Lys Glu Thr Arg Asp Trp Ala
                565                 570                 575

Arg Arg Arg Gly Ser Asp Gly Ser Gln Leu Gly Ala Arg Gly Pro Glu
            580                 585                 590

Pro Gly Ser Glu Arg Gly Arg Ser Pro Ser Asn Asn Thr Gln Gln
        595                 600                 605

Tyr Pro His Asn Ser Val Gly Glu Asp Ser Asp Gln Gly Asn Asp Gly
        610                 615                 620

Ser Asp Ser Arg
625

<210> SEQ ID NO 3
<211> LENGTH: 637
<212> TYPE: PRT
<213> ORGANISM: Drosophila melanogaster
```

<400> SEQUENCE: 3

```
Met Asn Glu Thr Glu Cys Glu Asp Leu Ile Lys Ser Val Lys Trp Thr
1               5                   10                  15
Glu Pro Ala Asn Leu Ile Ser Leu Ala Val Leu Glu Phe Ile Asn Val
            20                  25                  30
Leu Val Ile Gly Gly Asn Cys Leu Val Ile Ala Ala Val Phe Cys Ser
        35                  40                  45
Asn Lys Leu Arg Ser Val Thr Asn Phe Phe Ile Val Asn Leu Ala Val
    50                  55                  60
Ala Asp Leu Leu Val Gly Leu Ala Val Leu Pro Phe Ser Ala Thr Trp
65                  70                  75                  80
Glu Val Phe Lys Val Trp Ile Phe Gly Asp Leu Trp Cys Arg Ile Trp
                85                  90                  95
Leu Ala Val Asp Val Trp Met Cys Thr Ala Ser Ile Leu Asn Leu Cys
            100                 105                 110
Ala Ile Ser Leu Asp Arg Tyr Val Ala Val Thr Arg Pro Val Thr Tyr
        115                 120                 125
Pro Ser Ile Met Ser Thr Lys Lys Ala Lys Ser Leu Ile Ala Gly Ile
    130                 135                 140
Trp Val Leu Ser Phe Phe Ile Cys Phe Pro Pro Leu Val Gly Trp Lys
145                 150                 155                 160
Asp Gln Lys Ala Val Ile Gln Pro Thr Tyr Pro Lys Gly Asn His Thr
                165                 170                 175
Leu Tyr Tyr Ile Thr Thr Met Ser Ser Ser Glu Asp Gly Gln Leu Gly
            180                 185                 190
Leu Asp Ser Ile Lys Asp Gln Gly Glu Ala Ser Leu Pro Pro Ser Pro
        195                 200                 205
Pro His Ile Gly Asn Gly Asn Ala Tyr Asn Pro Tyr Asp Pro Gly Phe
    210                 215                 220
Ala Pro Ile Asp Gly Ser Ala Glu Ile Arg Ile Ala Ala Ile Asp Ser
225                 230                 235                 240
Thr Ser Thr Ser Thr Thr Ala Thr Thr Thr Thr Ala Ser Ser Ser
                245                 250                 255
Ser Thr Thr Glu Thr Glu Met Asp Leu Asp Leu Ile Asn Ala Pro Pro
            260                 265                 270
Gln Asn Arg Pro Gln Thr Ile Ser Gly Ser Cys Pro Trp Lys Cys Glu
        275                 280                 285
Leu Thr Asn Asp Arg Gly Tyr Val Leu Tyr Ser Ala Leu Gly Ser Phe
    290                 295                 300
Tyr Ile Pro Met Phe Val Met Leu Phe Phe Tyr Trp Arg Ile Tyr Arg
305                 310                 315                 320
Ala Ala Val Arg Thr Thr Arg Ala Ile Asn Gln Gly Phe Lys Thr Thr
                325                 330                 335
Lys Gly Ser Pro Arg Glu Ser Gly Asn Asn Arg Val Asp Glu Ser Gln
            340                 345                 350
Leu Ile Leu Arg Ile His Arg Gly Arg Pro Cys Ser Thr Pro Gln Arg
        355                 360                 365
Thr Pro Leu Ser Val His Ser Met Ser Ser Thr Leu Ser Val Asn Ser
    370                 375                 380
Asn Gly Gly Gly Gly Ala Val Ala Ser Gly Leu Gly Ala Ser Thr
385                 390                 395                 400
Glu Asp His Leu Gln Gly Gly Ala Pro Lys Arg Ala Thr Ser Met Arg
```

```
            405                 410                 415
Val Cys Arg Gln Arg His Glu Lys Val Ala Ile Lys Val Ser Phe Pro
            420                 425                 430

Ser Ser Glu Asn Val Leu Asp Ala Gly Gln Gln Pro Gln Ala Ser Pro
            435                 440                 445

His Tyr Ala Val Ile Ser Ser Ala Asn Gly Arg Arg Ala Ser Phe Lys
            450                 455                 460

Thr Ser Leu Phe Asp Ile Gly Glu Thr Thr Phe Asn Leu Asp Ala Ala
465                 470                 475                 480

Ala Ser Gly Pro Gly Asp Ile Glu Thr Gly Leu Ser Thr Thr Ser Leu
                485                 490                 495

Ser Ala Lys Lys Arg Ala Gly Lys Arg Ser Ala Lys Phe Gln Val Lys
            500                 505                 510

Arg Phe Arg Met Glu Thr Lys Ala Ala Lys Thr Ile Ala Ile Ile Val
            515                 520                 525

Gly Gly Phe Ile Val Cys Trp Leu Pro Phe Phe Thr Met Tyr Leu Ile
            530                 535                 540

Arg Ala Phe Cys Asp His Cys Ile Gln Pro Thr Val Phe Ser Val Leu
545                 550                 555                 560

Phe Trp Leu Gly Tyr Cys Asn Ser Ala Ile Asn Pro Met Ile Tyr Ala
                565                 570                 575

Leu Phe Ser Asn Glu Phe Arg Ile Ala Phe Lys Arg Ile Val Cys Arg
            580                 585                 590

Cys Val Cys Thr Arg Ser Gly Phe Arg Ala Ser Glu Asn Phe Gln Met
            595                 600                 605

Ile Ala Ala Arg Ala Leu Met Ala Pro Ala Thr Phe His Lys Thr Ile
            610                 615                 620

Ser Gly Cys Ser Asp Asp Gly Glu Gly Val Asp Phe Ser
625                 630                 635
```

<210> SEQ ID NO 4
<211> LENGTH: 26
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (12)..(12)
<223> OTHER INFORMATION: n at position 12 can be c or t
<220> FEATURE:
<221> NAME/KEY: misc_feature
<222> LOCATION: (16)..(16)
<223> OTHER INFORMATION: n at position 16 can be c or t
<220> FEATURE:
<221> NAME/KEY: misc_feature
<222> LOCATION: (17)..(17)
<223> OTHER INFORMATION: n at position 17 can be g or t
<220> FEATURE:
<221> NAME/KEY: misc_feature
<222> LOCATION: (18)..(18)
<223> OTHER INFORMATION: n at position 18 can be a, c, g or t
<220> FEATURE:
<221> NAME/KEY: misc_feature
<222> LOCATION: (21)..(21)
<223> OTHER INFORMATION: n at position 21 can be a, c, g or t

<400> SEQUENCE: 4
tacaagcttt gntggnnncc nttctt                                    26

<210> SEQ ID NO 5
<211> LENGTH: 29

```
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (15)..(15)
<223> OTHER INFORMATION: n at position 15 can be a, c, g or t
<220> FEATURE:
<221> NAME/KEY: misc_feature
<222> LOCATION: (16)..(16)
<223> OTHER INFORMATION: n at position 16 can be a or c
<220> FEATURE:
<221> NAME/KEY: misc_feature
<222> LOCATION: (17)..(17)
<223> OTHER INFORMATION: n at position 17 can be a or c
<220> FEATURE:
<221> NAME/KEY: misc_feature
<222> LOCATION: (18)..(18)
<223> OTHER INFORMATION: n at position 18 can be a or g
<220> FEATURE:
<221> NAME/KEY: misc_feature
<222> LOCATION: (21)..(21)
<223> OTHER INFORMATION: n at position 21 can be a, c, g or t
<220> FEATURE:
<221> NAME/KEY: misc_feature
<222> LOCATION: (24)..(24)
<223> OTHER INFORMATION: n at position 24 can be a or c

<400> SEQUENCE: 5
catgcggccg ctttnnnnta nccnagcca                                        29

<210> SEQ ID NO 6
<211> LENGTH: 30
<212> TYPE: DNA
<213> ORGANISM: Artificial
<220> FEATURE:
<223> OTHER INFORMATION: Oligonucleotide

<400> SEQUENCE: 6
cagtagccca gccagaagag gacggagaag                                       30

<210> SEQ ID NO 7
<211> LENGTH: 30
<212> TYPE: DNA
<213> ORGANISM: Artificial
<220> FEATURE:
<223> OTHER INFORMATION: Oligonucleotide

<400> SEQUENCE: 7
gctggctgcc gttcttcacc atgtacctgg                                       30

<210> SEQ ID NO 8
<211> LENGTH: 35
<212> TYPE: DNA
<213> ORGANISM: Artificial
<220> FEATURE:
<223> OTHER INFORMATION: Oligonucleotide

<400> SEQUENCE: 8
caggaattca tgagggacgg ggttatgaac gctag                                 35

<210> SEQ ID NO 9
<211> LENGTH: 34
<212> TYPE: DNA
<213> ORGANISM: Artificial
<220> FEATURE:
<223> OTHER INFORMATION: Oligonucleotide

<400> SEQUENCE: 9
```

```
gcttctagat cacctggagt ccgatccatc gttg                            34

<210> SEQ ID NO 10
<211> LENGTH: 41
<212> TYPE: DNA
<213> ORGANISM: Artificial
<220> FEATURE:
<223> OTHER INFORMATION: Oligonucleotide

<400> SEQUENCE: 10
acagaattcg ccaccatgag ggacggggtt atgaacgcta g                    41

<210> SEQ ID NO 11
<211> LENGTH: 21
<212> TYPE: DNA
<213> ORGANISM: Artificial
<220> FEATURE:
<223> OTHER INFORMATION: Oligonucelotide

<400> SEQUENCE: 11
ttgacggcgc tcgaggacgt c                                          21

<210> SEQ ID NO 12
<211> LENGTH: 42
<212> TYPE: DNA
<213> ORGANISM: Artificial
<220> FEATURE:
<223> OTHER INFORMATION: Oligonucelotide

<400> SEQUENCE: 12
caggaattcg ccaccatgaa tgaaacagag tgcgaggatc tc                   42

<210> SEQ ID NO 13
<211> LENGTH: 33
<212> TYPE: DNA
<213> ORGANISM: Artificial
<220> FEATURE:
<223> OTHER INFORMATION: Oligonucleotide

<400> SEQUENCE: 13
aatgcggccg ctcagctgaa gtccacgccc tcg                             33
```

METHODS OF SCREENING TYRAMINE- AND OCTOPAMINE-EXPRESSING CELLS FOR COMPOUNDS AND COMPOSITIONS HAVING POTENTIAL INSECT CONTROL ACTIVITY

CROSS REFERENCES TO RELATED APPLICATIONS

This application claims priority from U.S. Provisional Application Ser. No. 60/554,968 filed Mar. 19, 2004, and is a continuation-in-part of commonly assigned and U.S. patent application Ser. No. 10/832,022 filed Apr. 26, 2004 (now U.S. Pat. No. 7,541,155). The entire disclosures contained in U.S. Provisional Application Ser. No. 60/554,968 and U.S. application Ser. No. 10/832,022 now U.S. Pat. No. 7,541,155 are incorporated herein by this reference.

FIELD OF THE INVENTION

The present invention relates to compounds, compositions and method for controlling insects.

BACKGROUND OF THE INVENTION

Animals have chemosensory and mechanosensory systems that recognize a large array of environmental stimuli, generating behavioral responses. Many behavioral studies have been conducted to understand the genetics of these systems. The olfactory system plays a crucial role in the survival and maintenance of species, particularly in insects.

Biogenic amines serve a neurotransmitter or neuromodulator role in the olfactory system. The biogenic amine, octopamine, has a prominent role in insects and other invertebrates as it is involved in the regulation of multiple physiological events, for example, effects on muscular systems, sensory organs, endocrine tissues as well as learning and behavior. Octopamine (OA) occurs in large amounts in the nervous systems of species representing the phylum Arthropoda, including the classes Insecta and Crustacea. OA has a broad spectrum of biological roles in insects acting as a neurotransmitter, neurohormone and neuromodulator. OA exerts its effects through interaction with at least four classes of membrane bound receptors that belong to the family of G-protein coupled receptors (GPCRs). All members of GPCRs share the common motif of seven transmembrane (TM) domains.

When a GPCR is activated, depending on its type and the protein to which it binds, changes in intracellular concentrations of cAMP, $Ca^{2+}$ or both often take place. Since changes in intracellular levels of cAMP or $Ca^{2+}$ are the most commonly found cellular responses to biogenic amine treatments (e.g., serotonin, dopamine, octopamine, etc.), they are used to functionally classify receptor subtypes. As a result of GPCR activation, intracellular cAMP levels can either be elevated or reduced. The cellular response strictly relies on the specificity of interaction between the receptor and the G protein (See e.g., Gudermann T, Kalkbrenner F, Schultz G. 1996, "Diversity and selectivity of receptor-G protein interaction," *Annu Rev Pharmacol Toxicol* 36: 429-459; and Gudermann T, Schoneberg T, Schultz G. 1997, "Functional and structural complexity of signal transduction via G-protein-coupled receptors," *Annu Rev Neurosci* 20: 399-427, both of which are incorporated herein by this reference). When the receptor binds to Gs-type protein, the activated Gas subunit will interact with adenylyl cyclase (AC) in the plasma membrane. This leads to an increase of AC activity and production of cAMP from ATP.

Several biogenic amine receptors are also known to inhibit AC activity. This effect is mediated by interaction of the receptor with inhibitory G protein (Gi). Interaction of AC with activated Gαi subunits most likely competes with binding of activated Gas subunits and thereby interferes with AC activation.

Another pathway that is activated by several biogenic amine receptors results in a rise of intracellular $Ca^{2+}$ levels. In such a scenario the amine-activated receptor binds to G proteins of the Gq/o family (See e.g., supra, Gudermann et al., 1996 and Gudermann et al., 1997). The activated Gαq/o subunits bind to and stimulate phospholipase C (PLC) activity. The enzyme hydrolyzes a membrane-bound substrate, phosphatidylinositol 4,5-bisphosphate which gives rise to two second messengers IP3 and DAG. After binding of IP3 to its receptors, the calcium channel pore is opened and $Ca^{2+}$ is released into the cytoplasm. $Ca^{2+}$ ions play a vital role in the regulation of many cellular functions by binding to members of large family of $Ca^{2+}$-binding proteins and/or directly controlling enzymatic or ion channel activities.

Multiple insect species have been utilized to understand the biological functions and pharmacological characteristics of octopamine receptors. Studies with *Periplaneta americana* (American cockroach) have provided insight into the pharmacology and second messenger signaling of octopamine through octopamine receptors. For example, octopamine has been found to activate adenylate cyclase in certain cells in this species. Furthermore, octopamine has been found to increase inositol triphosphates in certain cells in this species.

As the octopaminergic system is believed to be unique to invertebrate physiology, this pathway has been proposed to offer a target for invertebrate pesticides with potential for low vertebrate toxicity. Formamidine-like chemicals have been found to be octopaminergic agonists and inhibit the uptake of sodium-sensitive octopamine in certain insects; for example, the formamidine pesticides chlordimeform and demethylchloridimeform were found to target the octopamine signaling pathway in certain invertebrates, including *Periplaneta americana*. To provide insight into the design of octopamine agonists that could be used as potential insecticides, structure function analyses have been performed with 2-(arylimino) oxazolidines and 2-(substituted benzylamino)-2-oxazolines in regard to activation of the octopamine sensitive adenylate cyclase in certain cells in *Periplaneta Americana*. More recently, it has been suggested that one site of action for the insecticidal activity of plant essential oils against *Periplaneta americana* is the octopaminergic system and that octopamine receptors may be targeted by these compounds, as described in Enan, E., 2001, "Insecticidal activity of essential oils: octopaminergic sites of action," *Comp. Biochem. Physiol. C Toxicol. Pharmacol.* 130, 325-327, which is incorporated herein by this reference.

Identifying plant essential oils and combinations thereof, having insect-controlling activity is particularly desirable given that many such compounds do not produce unwanted or harmful affects on humans, other animal species, and certain plants. However, identifying the most effective plant essential oils and combinations thereof requires random selection and use of tedious screening methods, which, given the vast number of plant essential oils and possible combinations thereof, is a substantially impossible task.

As such, there is a need in the art for an improved method for screening compounds and compositions for insect control activity.

SUMMARY OF THE PRESENT INVENTION

The present invention addresses the above identified problems, and others, by providing a screening method for identifying compounds and compositions that are effective insect control agents; a screening method for identifying compounds and compositions that are effective species-specific insect control agents; compounds and compositions isolated from the screening methods; cell lines expressing an octopamine receptor; and isolated nucleic acid molecule sequences.

DESCRIPTION OF THE DRAWINGS

FIG. 1A is an alignment of the nucleic acid sequence and the translated amino acid sequence from Pa $oa_1$, of SEQ ID NO: 1 and SEQ ID NO: 2;

FIG. 1B is the nucleic acid sequence from Pa $oa_1$ of SEQ ID NO: 1, with the seven putative transmembrane domains (TM) overlined and numbered 1 through 7, the stop codons (SC) underlined, and the initiation codon (M) underlined;

FIG. 2 is an alignment of the translated amino acid sequences of Pa $oa_1$ of SEQ ID NO: 2 and OAMB of SEQ ID NO: 3, with the seven putative transmembrane domains (TM) overlined and numbered 1 through 7;

FIG. 4 is a hydropathy profile of Pa $oa_1$ with the transmembrane domains (TM) numbered 1 through 7;

DETAILED DESCRIPTION OF THE INVENTION

Figure 3A:
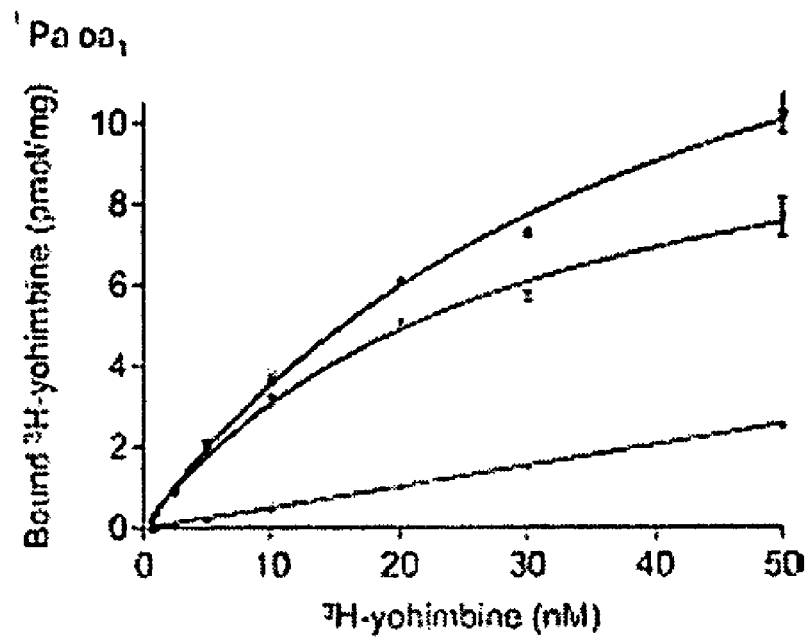
FIG. 3A is saturation binding curve of $^3$-H-yohimbine to Pa $oa_1$, where total binding is designated by the squares, nonspecific binding is designated by the triangle, and specific binding is designated by the inverted triangle.

The present invention includes: a screening method for identifying compounds and compositions that are effective insect control agents; a screening method for identifying compounds and compositions that are effective species-specific insect control agents; compounds and compositions isolated from the screening methods; transfected cell lines; and isolated nucleic acid molecule sequences.

Figure 1A:
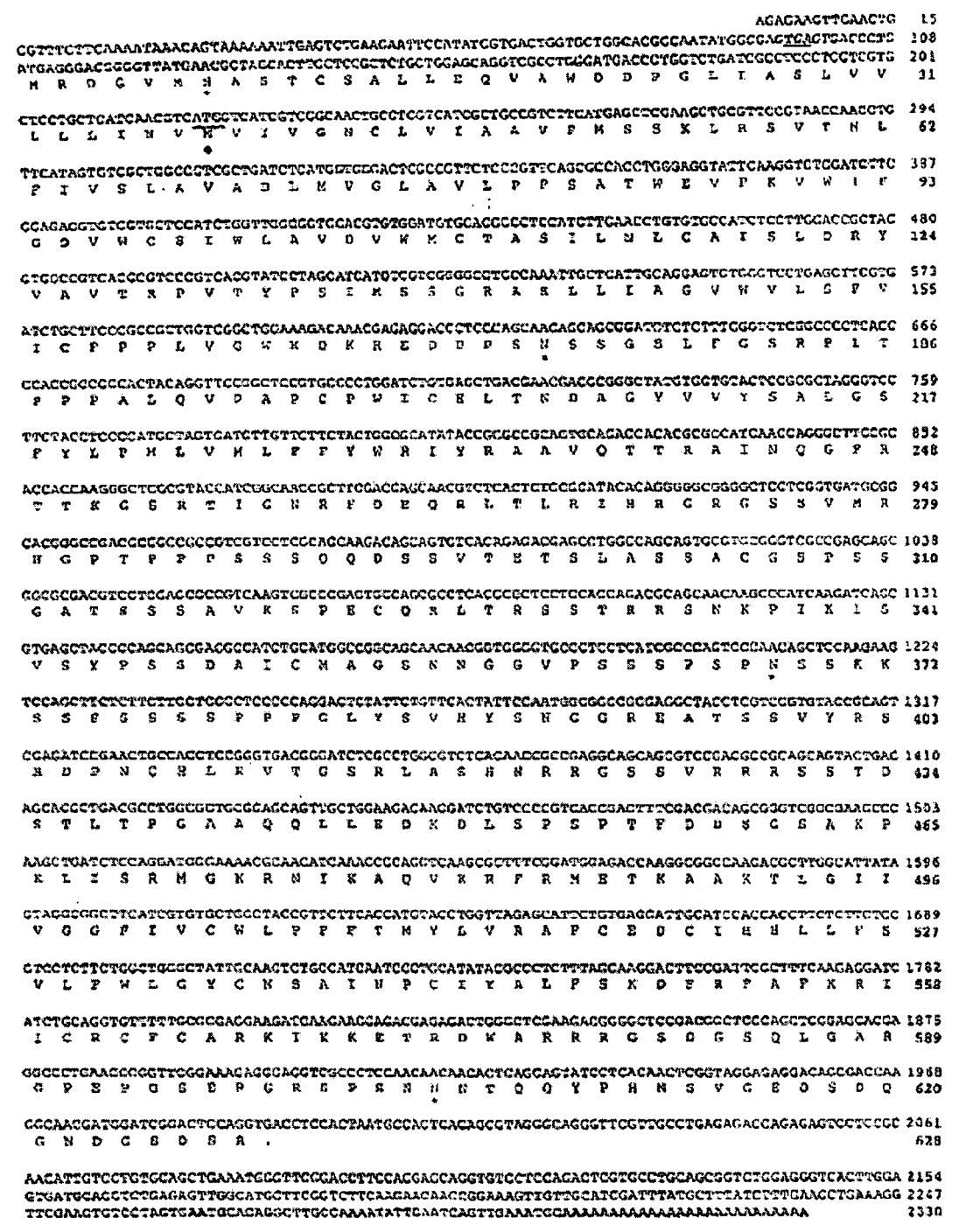

The present invention includes: an isolated nucleic acid molecule sequence which encodes a protein that binds a biogenic amine, resulting in changes in intracellular concentrations of cAMP, $Ca^{2+}$, or both, having a nucleotide sequence of SEQ ID NO: 1, or a fragment or derivative thereof and/or having an amino acid sequence of SEQ ID NO: 2, or a fragment or derivative thereof; an isolated nucleic acid molecule of having at least about 30% similarity to the nucleotide sequence of SEQ ID NO: 1, wherein the isolated nucleic acid molecule encodes a protein, resulting in changes in intracellular concentrations of cAMP, $Ca^{2+}$, or both; an isolated nucleic acid molecule of having at least about 30% similarity to the nucleotide sequence of SEQ ID NO: 1, wherein the molecule encodes an octopamine receptor or a protein having an amino acid sequence of SEQ ID NO: 2, or a fragment or derivative thereof; and an isolated nucleic acid molecule having a nucleotide sequence of SEQ ID NO: 1, or a fragment or derivative thereof, wherein the molecule encodes a protein designated Pa $oa_1$. SEQ ID NO: 1 and SEQ ID NO: 2 are shown in alignment in FIG. 1A and SEQ ID NO: 1 is also provided in FIG. 1B. Fragments and derivatives of the sequences shall include transmembrane domains (TM) 3, 5 and 6. Fragments and derivatives of the sequences may exclude, for example, portions upstream of TM 1, portions upstream of TM 2, or portions downstream of TM 7.

The present invention also includes: a strain of cells including a DNA vector having a nucleic acid sequence of SEQ ID NO: 1; a strain of cells expressing an octopamine receptor cloned from an insect species of interest; a strain of cells expressing an octopamine receptor cloned from *Periplaneta Americana* (Pa $oa_1$); a strain of cells expressing a protein having an amino acid sequence of SEQ ID NO: 2, or fragments or derivatives thereof, wherein the fragments or derivatives thereof bind octopamine; a strain of cells expressing an octopamine receptor cloned from *Drosophila melanogaster* (QAMB); a strain of cells expressing a protein having an amino acid sequence of SEQ ID NO: 3, or fragments or derivatives thereof, wherein the fragments or derivatives thereof bind octopamine. The transfected cells may be mammalian cells or insect cells; for example, they may be African green monkey kidney COS-7 cells (COS-7 cells) or human embryonic kidney-293 cells (HEK-293 cells).

The present invention also includes a screening method of using a cell line expressing an octopamine receptor to identify compounds and compositions that are effective insect control agents. For example, the octopamine receptor expressed by the cell line may be Pa $oa_1$; or have an amino acid sequence of SEQ ID NO: 2, or fragments or derivatives thereof, wherein the fragments or derivatives thereof bind octopamine.

The present invention also includes a method of using multiple cell lines, wherein the cell lines are transfected with octopamine receptors from different insect species of interest, to identify compounds and compositions that are effective species-specific insect control agents. For example, a cell line expressing Pa oa$_1$ and a cell line expressing OAMB could be used to screen compounds and compositions having insect control activity which is specific to *Periplaneta Americana* or to *Drosophila melanogaster*.

The present invention also includes compounds and compositions having the ability to control target insects, which compounds and/or compositions are identified using the screening methods of the present invention. These compounds and/or compositions may include compounds that are general regarded as safe (GRAS compounds) meaning that they do not produce unwanted or harmful affects on humans and other non-target animal species and that they are exempt from the Environmental Protection Agency's (EPA) pesticide registration requirements. The compounds and/or compositions of the present invention include certain plant essential oils identified using the screening methods of the present invention.

The compounds and compositions of the present invention control insects by targeting an octopamine receptor, resulting in a disruptive change in the intracellular levels of cAMP, $Ca^{2+}$ or both. For purposes of simplicity, the term insect has been and shall be used through out this application; however, it should be understood that the term insect refers, not only to insects, but also to arachnids, larvae, and like invertebrates. Also for purposes of this application, the term "insect control" shall refer to repelling or killing an insect.

The present invention is further illustrated by the following specific but non-limiting examples.

EXAMPLE 1

Preparation of Stably Transfected COS-7 Cell Lines and HEK-293 Cell Lines with Octopamine Receptor A. Isolation of a cDNA Encoding a G-Protein-Coupled Receptor From *Periplaneta americana*

G protein-coupled receptors from insects and a tick that are demonstrated to be octopamine receptors or have significant DNA similarity to known octopamine receptors are aligned using the program DNAStar (Ma). The following degenerate oligonucleotides are designed based on this alignment: Transmembrane (TM) VI oligonucleotide 5'TACAAGCTT TG(C,T)TGG(C,T)(G,T)(A,C,G,T)CC(A,C,G,T)TTCTT3' (SEQ ID NO: 4), and TM VII oligonucleotide 5'CATGCG-GCCGCTTT(A,C,G,T)(A,C)(A,C)(A,G)TA(A,C,GT)CC (A,C)AGCCA3' (SEQ ID NO: 5). The underlined sequence corresponds to the TM regions.

The TM VI oligonucleotide contains a HindIII site and the TM VII oligonucleotide contains a NotI site flanking the TM sequences Total RNA from the heads of mixed sex adult American cockroaches that have the antennae excised is prepared by ultracentrifugation through cesium chloride, as described in Chirgwin et al., 18 *Biochemistry* 5294-5299 (1979), and is reverse transcribed into cDNA using random hexamers and murine leukemia virus reverse transcriptase (Applied Biosystems, Foster City, Calif.). The polymerase chain reaction (PCR) is performed on this cDNA using AmpliTaq polymerase (Applied Biosystems) and the TM VI and VII oligonucleotides at final concentrations of about 5 µM The reaction conditions are about 95° C., about 5 min for about one cycle; about 95° C., about 45 s, about 40° C., about 2 min, about 72° C., about 30 s for about three cycles; about 95° C., about 45 s, about 55° C., about 2 min; about 72° C., about 30 s for about 37 cycles; and about 72° C., about 10 min for about one cycle.

Products are digested with HindIII and NotI and ligated into pBK-RSV (Stratagene, La Jolla, Calif.). Inserts are sequenced and compared to known genes by searching the NCBI database with the Blast program.

To obtain the corresponding cDNA for an approximately 101 nucleotide fragment with the highest similarity to octopamine receptors from other species, 5' and 3' rapid amplification of cDNA ends (RACE) are performed using the SMART RACE cDNA amplification system (Clontech, Palo Alto, Calif.). Poly(A) RNA is prepared from total RNA isolated from the head of *Periplaneta americana* using an oligo-dT column as per the manufacturer's protocol (Amersham Biosciences, Piscataway, N.J.). The poly(A) RNA is used as template in the RACE reverse transcription reaction for production of 5' and 3' RACE cDNA as per the manufacturer's instructions The gene specific oligonucleotides used for the RACE PCR are 5' RACE oligonucleotide 5'CAGTAGC-CCAGCCAGAAGAGGACGGAGAAG3' (SEQ ID NO: 6), and 3' RACE oligonucleotide 5'GCTGGCTGCCGTTCT-TCACCATGTACCTGG3' (SEQ ID NO: 7). 5' RACE and 3' RACE polymerase chain reactions are each about 50 µl and consist of about 2.5 µl of the respective cDNA reaction, about 0.2 µM of the gene specific oligonucleotide and the additional RACE components including Advantage 2 polymerase as per the manufacturer (Clontech). The cycling conditions for the 5' RACE are about 95° C., about 1 min for about one cycle; about 94° C., about 20 s, about 72° C., about 3 min for about five cycles; about 94° C., about 20 s, about 70° C., about 10 s, about 72° C., about 3 min for about five cycles; about 94° C., about 20 s, about 68° C., about 10 s, about 72° C., about 3 min for about 32 cycles; and about 72° C., about 10 min for about one cycle.

An approximately 1.9 kb product is gel purified and further, amplified using the same oligonucleotides, Advantage 2 polymerase and cycling parameters of about 95° C., about 3 min for about one cycle; about 94° C., about 20 s, about 68° C., about 10 s, about 72° C., about 3 min for about 35 cycles; and about 72° C., about 10 min for about one cycle. To facilitate T/A ligation, the product is A-tailed by precipitating with ethanol, resuspending in 1×PCR Buffer II (Applied Biosystems), 2 mM $MgCl_2$, 1 mM dATP and 0.05 U AmpliTaq per µl and incubating at about 72° C. for about 15 min The PCR product is ligated into pBK-RSV (Stratagene) that has been digested with SmaI and T-tailed using dTTP and Ampli-Taq. The insert is sequenced on both strands by automated fluorescent DNA sequencing (Vanderbilt Cancer Center).

The cycling conditions for the 3' RACE reaction are about 95° C., about 1 min for about one cycle; about 94° C., about 5 s, about 72° C., about 3 min for about five cycles; about 94° C., about 5 s, about 70° C., about 10 s, about 72° C., about 3 min for about five cycles; about 94° C., about 5 s, about 68° C., about 10 s, about 72° C., about 3 min for about 32 cycles; and about 72° C., about 10 min for about one cycle. The product of this reaction is A-tailed, subcloned and sequenced as for the 5' RACE product.

B. Generation of the Open Reading Frame for Octopamine Receptor (Pa oa$_1$)

Oligonucleotides used to amplify the open reading frame are a sense oligonucleotide 5' CAGGAATTC ATGAGGGACGGGGTTATGAACGCTAG 3' (SEQ ID NO: 8), and an antisense oligonucleotide 5' GCTTCTAGA TCACCTGGAGTCCGATCCATCGTTG 3' (SEQ ID NO: 9). Sequences corresponding to the open reading frame are underlined. The sense oligonucleotide contains an EcoRI restriction site and the antisense oligonucleotide an XbaI restriction site. These oligonucleotides are used in a polymerase chain reaction that included the 5'RACE cDNA as template and VENT polymerase (New England Biolabs, Beverly, Mass.).

The product is subcloned into the plasmid pAc5.1/V5-His (Invitrogen Life Technologies, Carlsbad, Calif.) at the EcoRI and XbaI restriction sites and sequenced. This plasmid is designated pAc-Pa oa$_1$. For mammalian cell expression, a Kozak sequence is inserted using a sense oligonucleotide 5'ACAGAATTCGCCACCATGAGGGACGGGGTTATGA ACGCTAG 3' (SEQ ID NO: 10) and an internal antisense oligonucleotide that contains an XhoI site 5' TTGACG-GCGCTCGAGGACGTC 3' (SEQ ID NO: 11). The sense oligonucleotide contains an EcoRI site These oligonucleotides are used in a polymerase chain reaction that includes pAc-Pa oa$_1$ as template and VENT polymerase. The product is inserted at EcoRI and XhoI sites into pAc-Pa oa$_1$, in which the corresponding EcoRI and XhoI fragment have been removed The product is sequenced. The entire open reading frame is then transferred into pCDNA3 (Invitrogen Life Technologies, Carlsbad, Calif.) at EcoRI and ApaI restriction sites, and this plasmid is designated pCDNA3-Pa oa$_1$.

C. Amplification and Subcloning of OAMB, an Octopamine Receptor from the Fruit Fly, *Drosophila melanogaster*

The *Drosophila melanogaster* head cDNA phage library GH is obtained through the Berkeley *Drosophila* Genome Project (world wide web <dot> fruitfly <dot> org). Phage DNA is purified from this library using a liquid culture lysate as described in Lech, *Current Protocols in Molecular Biology*, John Wiley & Sons, Inc., pp. 1 (2001). Oligonucleotides designed to amplify the open reading frame of *Drosophila melanogaster* OAMB consist of the sense oligonucleotide 5' CAGGAATTCGCCACCATGAATGAAACAGAGTGCGA GGATCTC 3' (SEQ ID NO: 12) and the antisense oligonucleotide 5' AATGCGGCCGCTCAGCTGAAGTCCACGCCC TCG 3' (SEQ ID NO: 13). Sequences corresponding to the open reading frame are underlined. A Kozak sequence is included in the sense oligonucleotide. In addition, the 5' oligonucleotide includes an EcoRI restriction site and the 3' oligonucleotide a NotI site.

For amplification by the polymerase chain reaction, about 200 ng of the GH library DNA is used as template with about 0.5 µM of each oligonucleotide and VENT DNA polymerase (New England Biolabs). Cycling conditions are about 95° C., about 5 min for about one cycle; about 95° C., about 30 s and about 70° C., about 1.5 min for about 40 cycles; and about 70° C., about 10 min for about one cycle. The product is digested with EcoRI and NotI, ligated into pCDNA3 and sequenced on both strands by automated fluorescent DNA sequencing (Vanderbilt Cancer Center).

D. Isolation of cDNA Encoding Octopamine Receptor (Pa oa$_1$)

A polymerase chain reaction with degenerate oligonucleotides corresponding to regions of TM VI and TM VII of previously identified octopamine receptors is used to isolate an approximately 101 nucleotide fragment of cDNA from the head of *Periplaneta americana* This cDNA fragment is used to design gene specific oligonucleotides to amplify the full-length cDNA of the corresponding gene by RACE. This method generates overlapping 5' and 3' segments that include the original cDNA fragment from TM VI to TM VII indicating these segments originate from the same cDNA. The cDNA includes an approximately 1887 nucleotide open reading frame and 5' and 3' untranslated regions (Genbank accession number is AY333178). The predicted initiation codon is preceded by an in-frame stop codon, indicating that the 5' end of the open reading frame is included in the cDNA and that the encoded protein will be full length. This cDNA and encoded protein are designated Pa oa$_1$.

The open reading frame encodes a protein of approximately 628 amino acids with a predicted molecular mass of about 68,642 Da. Hydropathy analysis by the method described in Kyte et al., J. Mol. Biol. 157, 105-132 (1982), with a window of about nine amino acids indicates about seven potential transmembrane spanning domains. In addition, a protein BLAST search finds similarity of Pa oa$_1$ to the rhodopsin family of 7 transmembrane G protein-coupled receptors contained within the conserved domain database.

The BLAST analysis also indicates Pa oa$_1$, is most similar to other biogenic amine receptors. As mentioned above, all members of GPCRs share the common motif of seven transmembrane (TM) domains. Of these seven domains, TM 3, 5 and 6 comprise the binding sites. Compared to proteins with defined functions, Pa oa$_1$ is most closely related to OAMB, an octopamine receptor from the fruit fly *Drosophila melanogaster* and to Lym-oa$_1$, an octopamine receptor from the pond snail *Lymnaea stagnalis*). Sequence similarity is also detected with vertebrate α1A adrenergic receptors and invertebrate tyramine receptors. Protein alignment indicates Pa oa$_1$ is about 51% identical to OAMB, 37% identical to Lym oa$_1$, and about 27% identical to both the insect tyramine receptors Tyr-Loc from *Locusta migratoria* and Tyr-Dro from *Drosophila melanogaster*. Sequence conservation between Pa oa$_1$, OAMB and Lym oa$_1$, is greatest within the TM domains, as shown in FIG. 2. The regions of lowest similarity among these three proteins are in the amino terminus extending into TM 1, extracellular loop 2 (between TM IV and V), intracellular loop 3 (between TM V and VI) and the carboxyl termini following TM VII.

E. Cell Culture and Transfection of Cells

Cell culture reagents may be obtained from Sigma-Aldrich (St. Louis, Mo.), or as otherwise indicated. African green monkey kidney COS-7 cells and human embryonic kidney (HEK)-293 cells are obtained from American Type Culture Collection (Manassas, Va.). COS-7 cells are grown in Dulbecco's modified Eagle's medium (about 4.5 g glucose/l) and about 10% fetal bovine serum. HEK-293 cells are grown in Dulbecco's modified Eagle's medium (about 1 g glucose/1), about 5% fetal bovine serum and about 5% newborn calf serum Both types of media are supplemented with about 100

U penicillin G/ml, about 100 µg streptomycin/ml and about 0.25 µg amphotericin B/ml) except during Lipofectamine 2000 transfections.

Lipofectamine 2000 and Opti-MEM I media may be obtained from Invitrogen Life Technologies (Carlsbad, Calif.). COS-7 cells are transiently transfected using Lipofectamine 2000. Cells are plated at about $1.5 \times 10^6$ cells per dish (about 55 cm$^2$) in about 10 ml growth medium without antibiotics the day before transfection. For each dish, about 30 µl Lipofectamine 2000 in about 1 ml Opti-MEM I medium is mixed with about 12 µg plasmid DNA in about 1 ml Opti-MEM I medium and added to the cells after an approximately 20 min incubation at room temperature. The cells are harvested for membrane preparation 24 h following transfection.

For stable transfections of HEK-293 cells, about $1 \times 10^6$ cells in about 2.5 ml growth media without antibiotics are plated into dishes (about 10 cm$^2$) the day before transfection. For transfection, about 10 µl Lipofectamine 2000 is added to about 250 µl Opti-MEM I medium. This is mixed with about 4 µg plasmid DNA in about 250 µl OptiMEM I medium. After an approximately 20 min incubation at room temperature, the approximately 500 µl of solution is added to cells in a single dish. Cells are split about 24 h after transfection into growth media containing about 0.8 mg G418 sulfate/ml (Mediatech Inc., Heradon, VA). Clonal lines are selected and assayed for receptor expression with whole cell binding by incubating about 500,000 cells in about 1 ml phosphate buffered saline (PBS; 137 mM NaCl, 2.7 mM KCl, 10 mM Na$_2$HPO$_4$, 1.4 mM KH$_2$PO$_4$ (pH 7.4)) with about 2 nM $^3$H-yohimbine for about 30 min at about 27° C. Cells are pelleted by centrifugation, washed with PBS, and then transferred to scintillation vials Nonspecific binding is determined by including about 50 µM phentolamine in the binding reaction.

F. Efficacy of Cells Lines Transfected with Octopamine Receptors for Screening Compounds and Compositions for Octopamine Receptor Interaction All steps are performed at about 4° C. or on ice. Cells are harvested in growth media by scraping from the dishes and then rinsing dishes with PBS. The cells are centrifuged at about 1000 g for about 3 min, washed with PBS and centrifuged again. The cells are suspended in ice cold hypotonic buffer (10 mM Tris-Cl (pH 7.4)), incubated on ice for about 10 min, and lysed using a glass dounce homogenizer and tight glass pestle (Kontes Glass Co., Vineland, NJ) with about 10 strokes Nuclei are pelleted by centrifugation at about 600 g for about 5 min The supernatant is decanted and centrifuged at about 30,000 g for about 30 min to pellet a crude membrane fraction. The pellet is suspended, in binding buffer (50 mM Tris-Cl, 5 mM MgCl$_2$ (pH 7.4)). Protein concentration is determined by the Bradford assay (Bio-Rad Laboratories, Hercules, Calif.). Membranes are frozen on dry ice and stored at about −75° C. in aliquots.

Antagonists and biogenic amines are obtained from Sigma-Aldrich (St. Louis, Mo.). Octopamine is the mixed isomeric form DL-octopamine. $^3$H-yohimbine is obtained from Perkin Elmer Life Sciences (Boston, Mass.). Radioligand binding is performed with about 7.5-15 µg membrane protein in about 250 µl binding buffer for about 30 min at about 27° C. while shaking at about 100 rpm. Reactions are terminated by addition of about 3 ml ice cold binding buffer and filtered over GF/C filters (Whatman International, Maidstone, England) that have been soaked for about 30 min in about 0.3% polyethylenimine (Sigma-Aldrich). Filters are rinsed again with about 3 ml binding buffer For the determination of $K_d$ and $B_{max}$, a range of $^3$H-yohimbine is used from about 0.5 to 50 nM, and about 50 µM phentolamine is used as a competitor to determine nonspecific binding. To determine $K_i$, of different ligands, about 2 nM $^3$H-yohimbine is used with a concentration range of competitor that gives from 0% to 100% competition. Binding data is analyzed by nonlinear regression using the software GraphPad Prism (San Diego, Calif.).

For pharmacological binding experiments, Pa oa$_1$, is expressed in COS-7 cells by transient transfection. Membrane fractions are analyzed to determine total, nonspecific and specific binding of $^3$H-yohimbine, as shown in FIG. 3A. The $K_d$ and $B_{max}$ for specific binding are determined to be about 28.4 nM and about 11.8 pmol/mg protein, respectively. Membrane fractions from COS-7 cells transiently transfected with empty pCDNA3 do not demonstrate specific binding. The high affinity binding of $^3$H-yohimbine by Pa oa$_1$ indicate that this is a suitable ligand to be used for competition binding experiments.

Figure 3B:
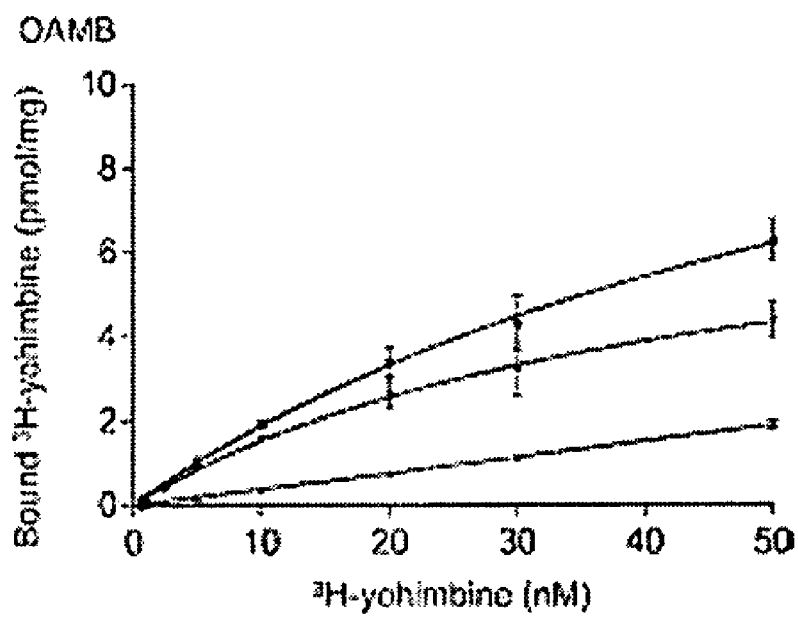
FIG. 3B is saturation binding curve of $^3$H-yohimbine to OAMB, where total binding is designated by the squares, nonspecific binding is designated by the triangle, and specific binding is designated by the inverted triangle.

The octopamine receptor OAMB from *Drosophila melanogaster* is amplified by the polymerase chain reaction. Saturation binding analysis with $^3$H-yohimbine is performed with OAMB expressed in COS-7 cells, as shown in FIG. 3B. The $K_d$ and $B_{max}$ are determined to be about 43.0 nM and about 8.04 pmol/mg, respectively.

Competitive binding with various biogenic amines is utilized to determine the affinities for potential natural ligands of Pa oa$_1$. Referring now to Table A, below, DL-Octopamine has the lowest $K_i$ (about 13.3 µM) for Pa oa$_1$ followed by tyramine (about 31.0 µM). The decreasing order of affinity for the biogenic amines is octopamine>tyramine>dopamine>serotonin. The binding affinities for octopamine and tyramine are determined for this receptor. The $K_i$ (mean±standard deviation) of octopamine and tyramine for OAMB are about 8.20±2.60M and about 33.8±7.93 µM, respectively. These values are similar to those obtained for Pa oa$_1$. The affinity of octopamine is about 2.3-fold higher than tyramine for Pa oa$_1$, and for OAMB, the affinity of octopamine is about 4.1-fold higher than tyramine, indicating that octopamine is the likely endogenous ligand for Pa oa$_1$.

TABLE A

| Ligand | $K_i$ (µM) |
| --- | --- |
| Biogenic Amine | |
| Octopamine | 13.3 ± 2.4 |
| Tyramine | 31.0 ± 1.9 |
| Dopamine | 56.6 ± 8.0 |
| Serotonin | 77.4 ± 11.6 |
| Antagonist | |
| Chlorpromazine | 0.012 ± 0.003 |
| Phentolamine | 0.023 ± 0.009 |
| Mianserin | 0.048 ± 0.013 |
| Metoclopramine | 4.76 ± 1.32 |

In addition to using the affinity of octopamine receptors for specific antagonists as a method for classifying these receptors, antagonists may be used to analyze the effects of octopamine on adenylate cyclase activity in the brain, ventral nerve cord and hemocytes of *Periplaneta americana*. A pharmacological profile is developed for Pa oa$_1$ using these antagonists. With reference to Table A, in order of decreasing affinity, the profile of the antagonists is chlorpromazine>phentolamine>mianserin>metoclopramide.

EXAMPLE 2

Structural Features of Cloned American Cockroach Octopamine Receptor (Pa $oa_1$)

Figure 1B:
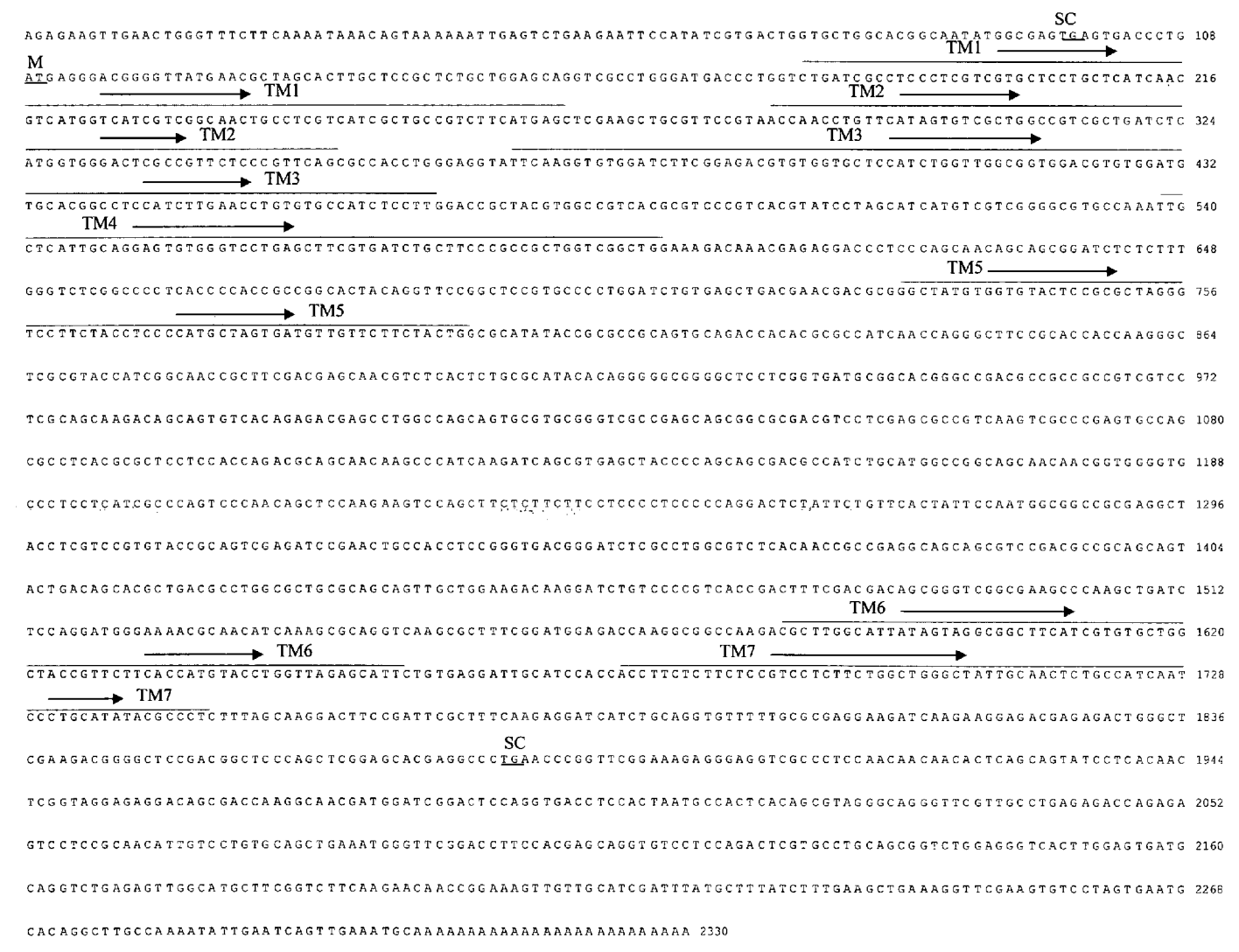

The Pa $oa_1$ cDNA of 2268 bp which includes an 1887 nucleotide open reading frame and 5' and 3' untranslated regions is set forth in FIGS. 1A, 1B and SEQ ID NO: 1. With reference to FIG. 1B, the predicted initiation codon (M) is preceded by an in-frame stop codon (SC). This indicates that the 5' end of the open reading frame is included in the cDNA and that the encoded protein would be full length.

Figure 5:
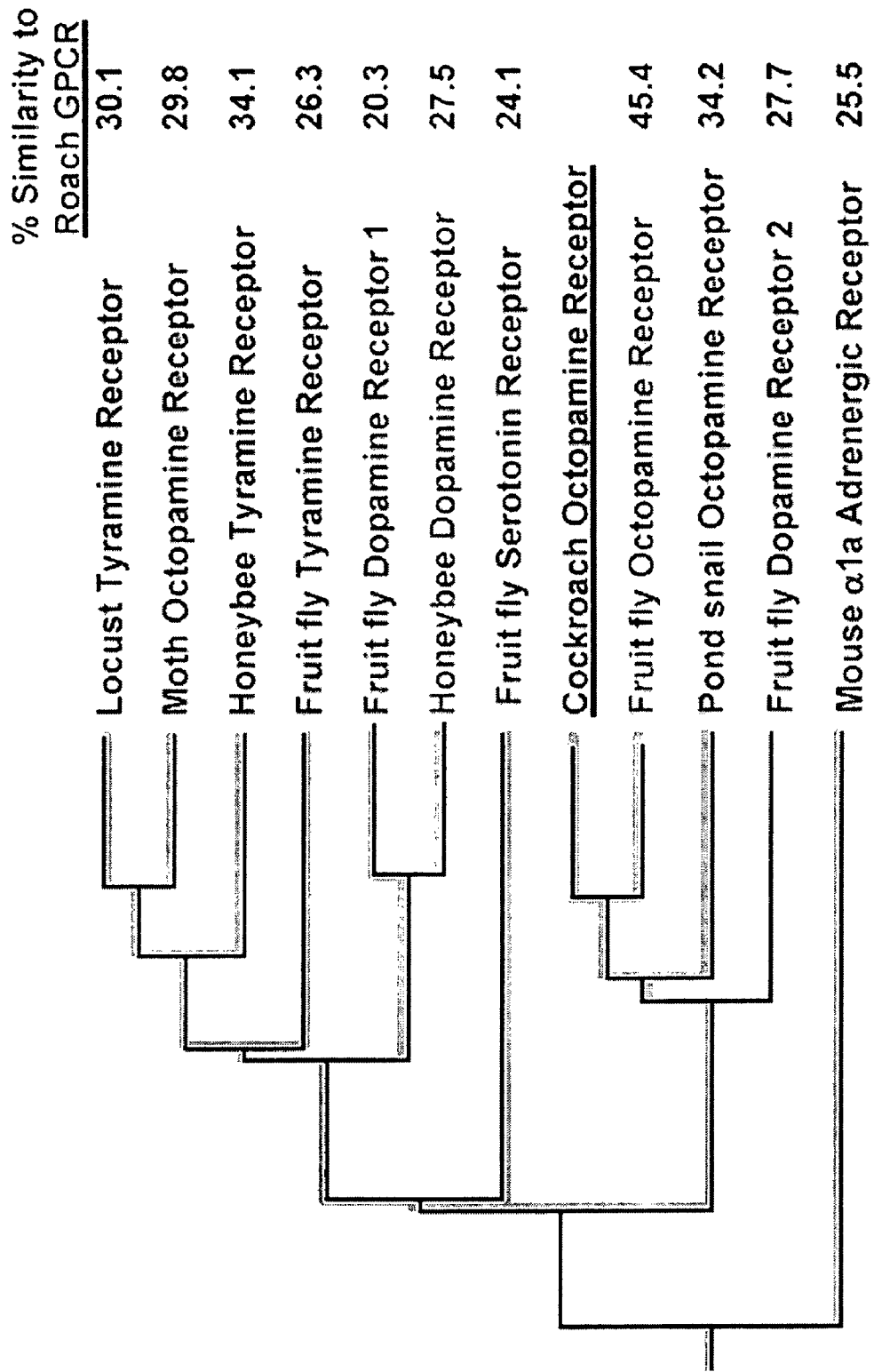
FIG. 5 depicts the similarity between octopamine and tyramine receptors from different insect species.

With reference to FIG. 4, hydropathy analysis by the method of Kyte and Doolittle with a window of 9 amino acids indicates that this sequence shares the common motif of 7 potential transmembrane scanning domains. See Kyte and Doolittle, 1982, *J. Mol. Biol.* 157, 105-132. A phylogenic comparison of invertebrate biogenic amine receptor sequences reveals that both OAMB and Pa $oa_1$ sequences share ~45% similarity, which is illustrated in FIG. 5. Pa $oa_1$ clusters with octopamine and tyramine receptors from different insect species. Similarity between these receptors is analyzed using BLAST search and calculated based on protein alignment using DNASTAR software program. Pa $oa_1$ is used as a reference for comparisons with other receptors.

With reference to FIG. 2, protein alignment indicates sequence conservation between Pa $oa_1$ and OAMB is greatest within the transmembrane domains (TMs). The regions of lowest similarity among these two proteins are in the amino terminus extending into TM1, extracellular loop2 between TM4 and TM5, intracellular loop between TM5 and TM6 and the carboxy termini following TM7.

EXAMPLE 3

Effects of Treatment with Octopamine on Cells Expressing the Octopamine Receptor (Pa $oa_1$)

A. Effect of Treatment on [cAMP]

Twenty-four hours before cell treatment, about 300,000 HEK-293 cells are plated in about 1 ml media with about 0.8 mg G418/ml into multi-well dishes (e.g., 12-well, 4.5 cm$^2$). For cell treatment, the media is aspirated and about 1 ml PBS with about 300 µM IBMX and the test reagent is added. Cells are incubated at about 37° C. for about 20 min, and the PBS is then aspirated. Cells are incubated with about 70% ethanol for about 1 h at about −20° C. The cellular debris is centrifuged and then the supernatant is removed and lyophilized to dryness. The amount of cAMP in the extract is determined by using a cAMP binding protein from the $^3$H-cAMP Biotrak assay system (Amersham Biosciences) as per the manufacturer's instructions. To test the effects of calcium chelation on cAMP levels, the cells are incubated with about 20 µl V 1 BAPTA/AM (Calbiochem Biochemicals, La Jolla, Calif.) for about 10 min before the addition of the test reagents.

Octopamine has been demonstrated to increase levels of the second messenger cAMP in brain, thoracic ganglion and hemocytes from *Periplaneta americana*. To determine which second messenger signaling pathways octopamine could affect through the Pa $oa_1$ receptor, HEK-293 cells are stably transfected with pCDNA3-Pa $oa_1$ or pCDNA3 without an insert as a control. In the control HEK-293 cells, neither DL-octopamine nor tyramine at concentrations up to about 100 µM has significant effects on cAMP levels.

Figure 6:
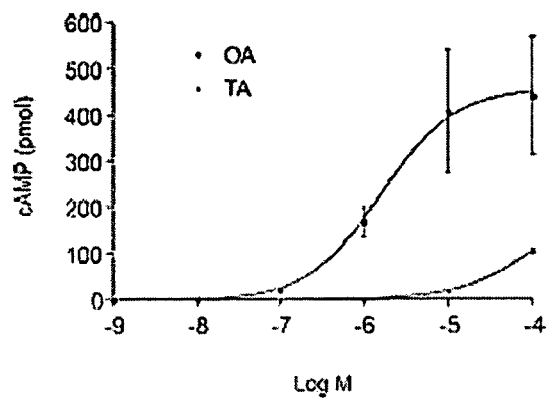
FIG. 6 is a graph depicting the change of intracellular cAMP levels in HEK-293 cells expressing Pa $oa_1$ in response to treatment with various concentrations of either octopamine (OA) or tyramine (TA)

A clone transfected with pCDNA3-Pa $oa_1$ having a high specific binding to $^3$H-yohimbine is selected for second messenger analysis. Both octopamine and tyramine are able to increase the levels of cAMP in these cells in a dose dependent manner, as shown in FIG. 6. The $EC_{50}$s for the octopamine and tyramine mediated increases in cAMP are about 1.62 and 97.7 µM, respectively (p<0.05). Octopamine is more potent than tyramine in the cAMP response as a statistically significant increase in cAMP over the basal level (about 0.48 pmol cAMP) is first detected with about 10 nM octopamine (about 1.2 pmol cAMP) (p<0.05). The cAMP concentration with about 10 nM tyramine is about 0.50 pmol cAMP, and therefore not statistically significant from the basal level (p>0.05). A concentration of about 1 µM tyramine results in an increase in cAMP to about 1.2 pmol. In addition, about 100 µM octopamine leads to an approximately 911-fold increase in cAMP compared to an approximately 215-fold increase for about 100 µM tyramine. Since these assays are performed in the presence of the phosphodiesterase inhibitor IBMX, the increases in cAMP is determined to be through activation of adenylate cyclase. As such, it appears that the Pa $oa_1$ receptor is an octopamine receptor, the Pa $oa_1$ receptor may be targeted to effect a disruptive change in intracellular levels of cAMP, controlled targeting of the receptor allows for insect control, and the cell lines stably expressing the Pa $oa_1$ receptor may be used to screen compounds and compositions for insect control activity.

B. Effect of Treatment on cAMP and [Ca$^{2+}$]

To determine cAMP levels in cells, about 24-hours before cell treatment, 300,000 HEK-293 cells are plated in 1 mL media with 0.8 mg G418/mL into multi-dishes (4.5 cm2). For cell treatment, the media is aspirated and 1 mL PBS with 300 µM IBMX and the test reagent is added. Cells are incubated at 37° C. for 20 min, and the PBS is then aspirated. Cells are incubated with 70% ethanol for 1 hour at −20° C. The cellular debris is centrifuged and then the supernatant is removed and lyophilized to dryness. The amount of cAMP in the extract is determined by using a cAMP binding protein from the $^3$H-cAMP Biotrak assay system (Amersham Biosciences, Piscataway, N.J.) as per the manufacturer's instructions.

Figure 7:
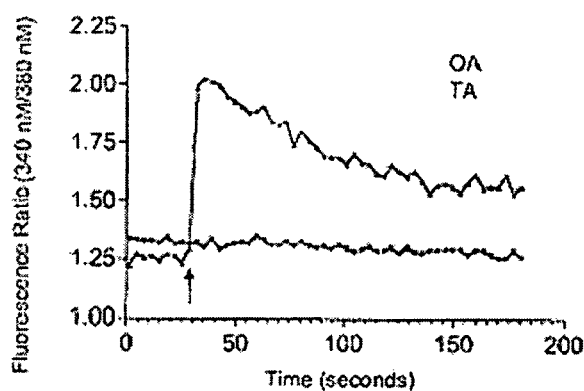
FIG. 7 is a graph depicting the change in intracellular calcium levels in HEK-293 cells expressing Pa $oa_1$ in response to treatment with either 100 nM octopamine (OA) or 100 nM tyramine (TA)

To determine Ca$^{2+}$ levels in the cells, HEK-293 cells are washed once with Hank's balanced salt solution (137 mM NaCl, 5.4 mM KCl, 0.3 mM Na$_2$HPO$_4$, 0.4 mM KH$_2$PO$_4$, 4.2 mM NaHCO$_3$, 1 mM CaCl$_2$, 1 mM MgSO$_4$, and 5.6 mM glucose (pH 7.4)) (HBSS). Cells are collected by scraping and are suspended at about 750,000 cells/ml in HBSS with about 5 µM Fura-2 AM (Sigma-Aldrich). Cells are incubated at about 37° C. for about 1 h in the dark, centrifuged, suspended in HBSS at about 750,000 cells/ml and used for calcium measurements A spectrofluorometer with Felix software from Photon Technology International (Lawrenceville, NJ) is used for the fluorescence measurements and data collection Octopamine has been demonstrated to modulate intracellular calcium levels in cultured hemocytes of *Malacosoma disstria*. Also, in hemocytes from *Periplaneta americana*, octopamine lead to an increase in inositol triphosphate which likely will lead to increases in calcium in these cells as well The ability of both octopamine and tyramine to modulate calcium levels in the HEK-293 clone expressing Pa $oa_1$ is determined Neither about 10 µM octopamine nor about 10 µM tyramine modulates intracellular calcium levels in control HEK-293 cells transfected with pCDNA3 lacking an insert However, when about 100 nM octopamine is added to the Pa oa₁ expressing HEK-293 cells, a rapid increase in intracellular calcium is detected, as shown in FIG. 7. In these same cells, about 100 nM tyramine does not modulate intracellular calcium levels, as shown in FIG. 7.

Testing of these amines at additional concentrations indicates that the lowest concentration of octopamine that increases intracellular calcium levels is about 10 nM Tyramine is found to increase intracellular calcium when a concentration of about 1 µM or higher is tested These increases in intracellular calcium by about 10 nM octopamine and about 1 µM tyramine are to a similar level, both of which is lower than the increase in calcium mediated by about 100 nM octopamine. This result is similar to that obtained with the cAMP assay in that an approximately 100-fold increase in tyramine concentration compared to about 10 nM octopamine is required to give a similar level of response.

As such, it appears that the Pa oa₁ receptor is an octopamine receptor, the Pa oa₁ receptor may be targeted to effect a disruptive change in intracellular levels of $Ca^{2+}$, controlled targeting of the receptor allows for insect control, and the cell lines stably expressing the Pa oa₁ receptor may be used to screen compounds and compositions for insect control activity.

Figure 8:
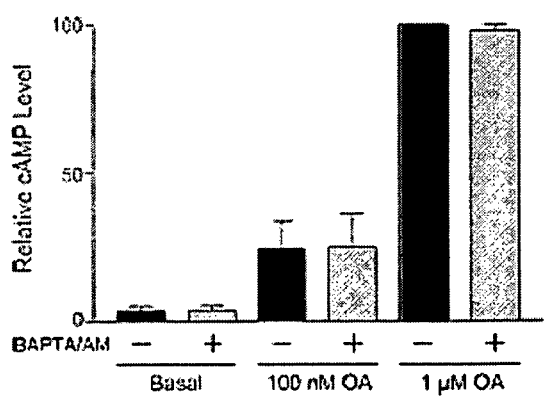
FIG. 8 is a bar graph depicting the change in intracellular cAMP levels in HEK-293 expressing Pa $oa_1$ in response to treatment with 0, 100 nM, or 1 µM octopamine (OA) in the presence and absence of 20 µM BAPTA/AM, a calcium chelator.

Octopamine is found to increase both cAMP and calcium in HEK-293 cells expressing Pa oa₁ and the calcium increase is detected immediately upon octopamine addition. As such, the possibility that calcium is leading to a secondary increase in cAMP levels in the cells expressing Pa oa₁ is tested. The intracellular calcium chelator BAPTA/AM is used BAPTA/AM at about 20 µM is found to inhibit the increase in free intracellular calcium when about 1 µM octopamine is added to the Pa oa₁-expressing cells. Octopamine-mediated changes in cAMP levels are compared in the absence and presence of about 20 µM BAPTA/AM. cAMP levels following treatment with either about 100 nM or about 1 µM octopamine, as well as basal cAMP levels, are not found to be statistically different, whether in the absence or presence of about 20 µM BAPTA/AM, as shown in FIG. 8. This indicates that the increase in cAMP by octopamine results from direct coupling of Pa oa₁ to a G protein that leads to activation of adenylate cyclase, making the expression of Pa oa₁ in HEK-293 cells a good model for adenylate cyclase-modulated insect control through this receptor and the cell lines stably expressing the Pa oa₁ receptor useful for screening compounds and compositions for insect control activity.

EXAMPLE 4

Receptor Binding and Changes in cAMP and Intracellular $Ca^{2+}$ in Response to Octopamine Treatment For radioligand binding studies, the binding of ³H-yohimbine to membranes isolated from COS-7 cells expressing Pa oa₁ and octopamine receptor (OAMB) from *Drosophila melanogaster* Are performed. See Bischof and Enan, 2004, *Insect Biochem. Mol. Biol.* 34, pp. 511-521, which is incorporated herein by this reference. The data shown in Table B demonstrates that the affinity of Pa oa₁ to the radioligand is about 1.5 fold higher than OAMB. Radioligand binding using ³H-yohimbine is performed on membranes expressing either either Pa oa₁ or OAMB. For the determination of $K_d$ and $B_{max}$, a range of ³H-yohimbine is used from 0.5 to 50 nM, and 50 µM phentolamine is used as a competitor to determine non-specific binding. To determine $K_i$ of octopamine, 4 nM ³H-yohimbine is used with a concentration range of octopamine that gives from 0 to 100% competition.

TABLE B

| OAR Species | Kd (nM) | $B_{max}$ (pmole receptor/ mg protein) | Ki (µM) |
| --- | --- | --- | --- |
| OAR species | 28.4 | 11.80 | 13.30 |
| OAMB | 43.0 | 8.04 | 8.20 |

Figure 9:
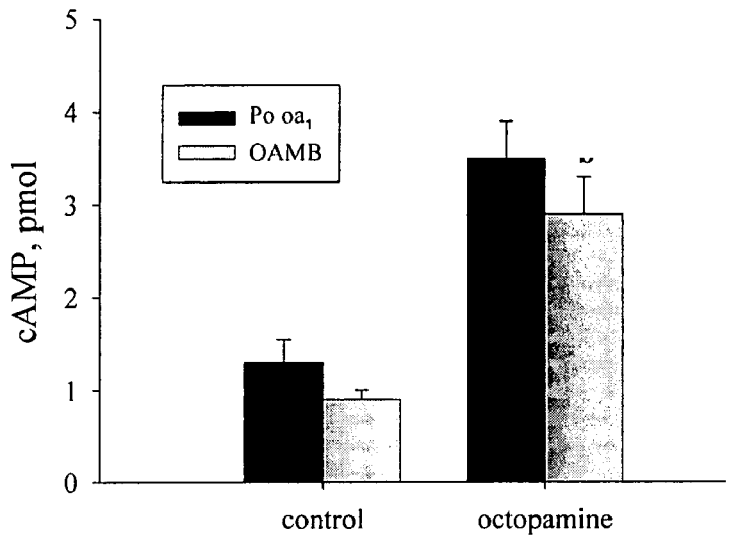
FIG. 9 is a bar graph depicting the cAMP response to octopamine through Pa $oa_1$ and OAMB expressed in HEK-293 cells where the cells expressing either receptor are treated with 10 µM octopamine and the level of cAMP is determined.
Figure 10A:
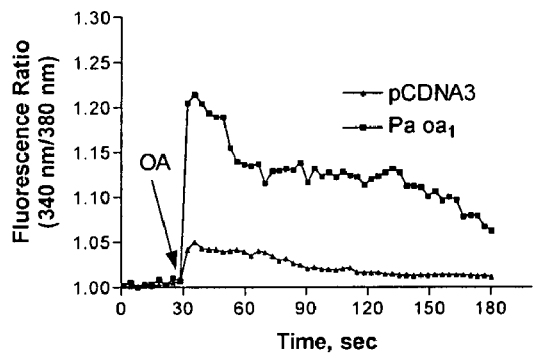
FIGS. 10A and 10B are graphs depicting the calcium response to octopamine through Pa $oa_1$ and OAMB, respectively, expressed in HEK-293 cells.
Figure 10B:
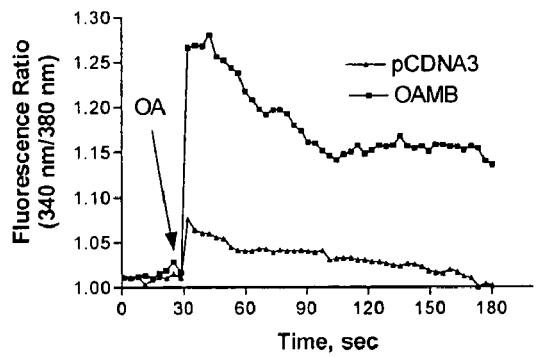

With reference to FIG. 9, OA (10 µM) increases the level of cAMP in HEK-293 cells permanently expressing either OAMB or Pa oa₁. With reference to FIGS. 10A and 10B, OA (10 µM) increases the level $[Ca^{2+}]_i$ in HEK-293 cells permanently expressing either OAMB or Pa oa₁, where HEK-293 cells expressing either receptor are incubated for 30 s before the addition of 10 µM octopamine (OA). The arrow in the figures indicates addition of the amine. The fluorescence ratio determined from excitation with 340 and 380 nm is plotted to indicate changes in $[Ca^{2+}]_i$ levels. These increases are mediated through the OAR as judged by the insignificant changes in cAMP level and $[Ca^{2+}]$ in cells transfected with an empty vector then treated with 10 µM OA (data not shown).

EXAMPLE 5

Effects of Treament with Plant Essential Oils on Cells Expressing the Octopamine Receptor In this example, membranes isolated from COS-7 cells expressing the receptor are used for receptor binding studies and HEK-293 cells are used for cAMP and $[Ca^{2+}]$ studies. Plant essential oils, including: p-cymene [methyl(1-methylethyl)benzene], eugenol [2-methoxy-4-(2-propenyl)phenol], trans-anethole [1-methoxy-4-(1-propenyl)benzene], cinnamic alcohol [3-phenyl-2-propen-1-ol], α-terpineol [p-menth-1-en-8-ol], methyl salicylate [2-hydroxybenzoic acid methyl ester], 2-phenylethyl propionate, and geraniol [3,7-dimethyl-2,6-octadien-1-ol], are obtained from City Chemical (West Haven, Conn.) and tested for insect control activity. The chemical structures of these compounds are set forth in FIG. 11.

A. Receptor Binding Activity

The binding activity of ³H-yohimbine to membranes expressing Pa oa₁ or OAMB is performed in the presence and absence of three structurally related plant essential oil monoterpenoids, which are selected based on their insecticidal activity, the absence or presence and location of the hydroxyl group and a spacing group within the molecule. Membrane protein (10 µg) expressing Pa oa₁ is incubated with 4 nM ³H-yohimbine in the presence and absence of 50 µM of the test chemical. The specific activity is calculated as the difference between counts in the presence and absence of test chemical. Specific binding is calculated by determining non-specific binding with 50 µM tested plant essential oils and subtracting nonspecific binding from total binding.

Figure 12:
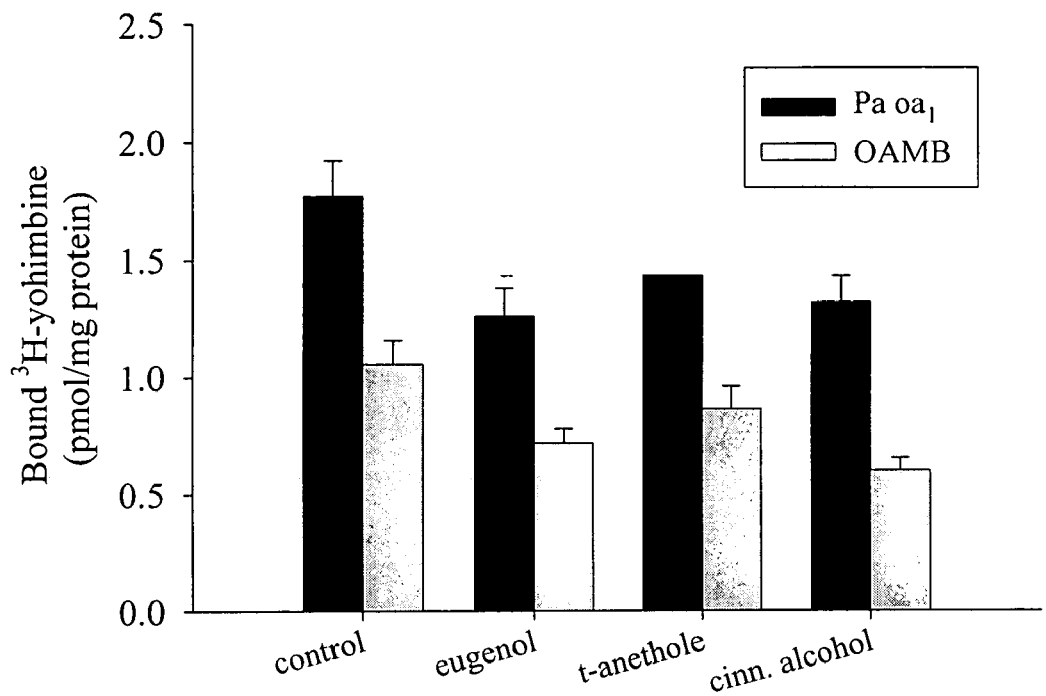
FIG. 12 is a bar graph depicting the effect of certain plant essential oils on specific binding of $^3$H-yohimbine to Pa $oa_1$ and OAMB.

With reference to FIG. 12, depicting specific binding of ³H-yohimbine to Pa oa₁ and OAMB, while eugenol and cinnamic alcohol decrease the binding of ³H-yohimbine to membranes expressing either Pa oa₁ or OAMB as compared to the corresponding control, trans-anethole decreases the ³H-yohimbine binding activity to only Pa oa₁. It is also found that eugenol and trans-anethole are more potent inhibitors against Pa oa₁ than OAMB, while cinnamic alcohol is more potent against OAMB than Pa oa₁. The data suggested insect species differences in receptor binding in response to monoterpenoids.

B. Effects of Treatment on [cAMP]

Figure 13:
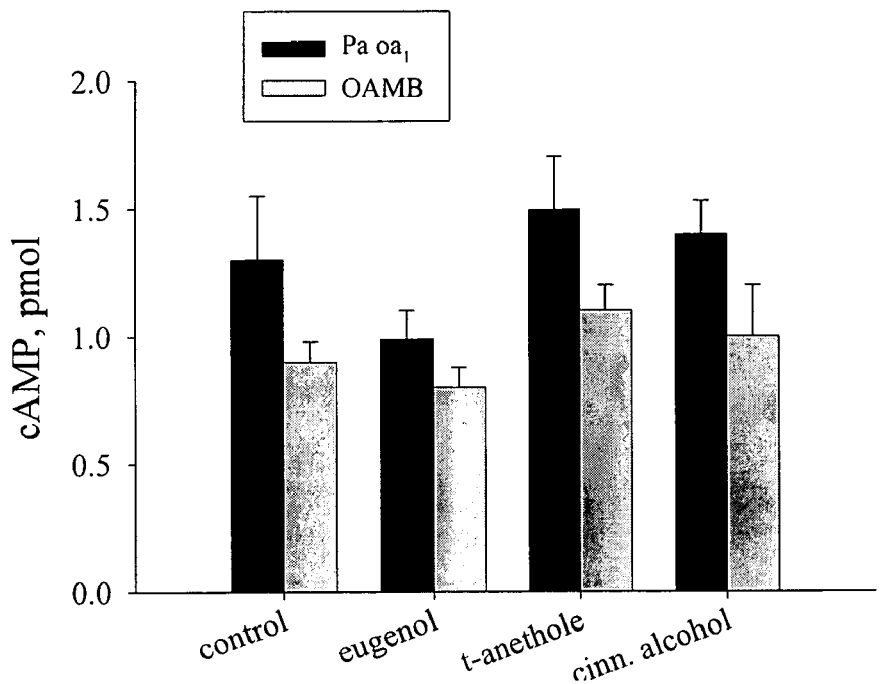
FIG. 13 is a bar graph depicting the effect of certain plant essential oils on cAMP levels in HEK-293 cells expressing either Pa $oa_1$ or OAMB.
Figure 14A:
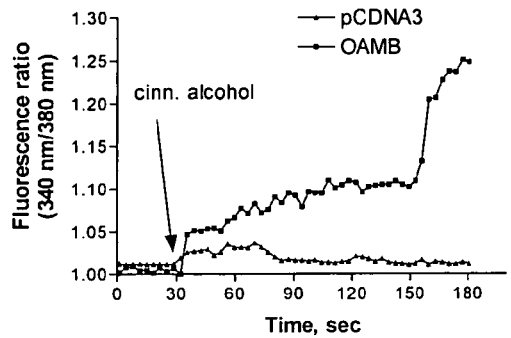
FIGS. 14A-14F are graphs depicting the effect of certain plant essential oils on intracellular calcium $[Ca^{2+}]_i$ levels in HEK-293 cells either transfected with Pa $oa_1$ or OAMB.
Figure 14B:
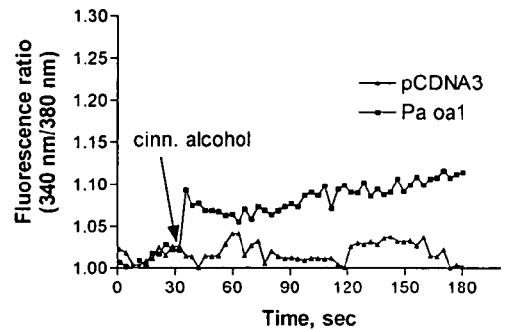
Figure 14C:
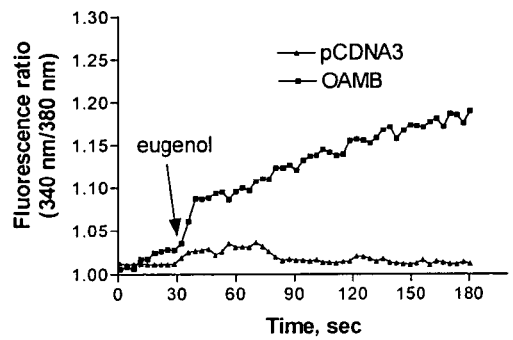
Figure 14D:
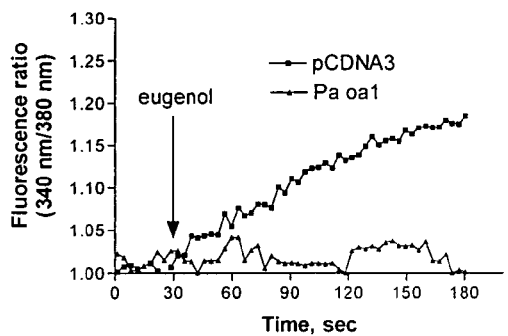
Figure 14E:
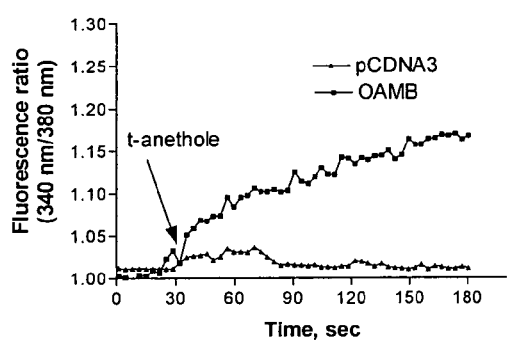
Figure 14F:
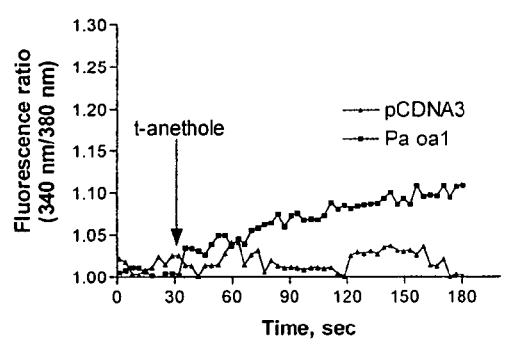

FIG. 13 depicts the effect of certain plant essential oils on cAMP levels in HEK-293 cells expressing either Pa $oa_1$ or OAMB. HEK-293 cells stably expressing either receptor are treated with 300 μM IBMX and the effect of tested plant essential oils (50 μM) on basal cAMP levels is measured.

Eugenol (50 μM) significantly decreases the cAMP level (24%) in cells expressing Pa $oa_1$ but slightly decreased cAMP level in cells expressing OAMB. A 22% increase in cAMP level in cells expressing OAMB is found in response to treatment with (50 μM) trans-anethole. Cinnamic alcohol (50 μM) induces slight increase in cAMP level in both cell models.

C. Effect of Treatment on Intracellular Calcium Mobilization

To address whether changes in $[Ca^{2+}]_i$ in octopamine receptor-expressing cells in response to 25 μM of tested plant essential oils is mediated specifically through the receptor, cells transfected with an empty plasmid (pCDNA3) are treated with either test chemicals or solvent only and changes in $[Ca^{2+}]_i$ are monitored. In cells transfected with an empty plasmid, none of the test chemicals induce remarkable changes in $[Ca^{2+}]_i$ levels as compared with cells treated with the solvent (data not shown).

On the other hand, changes in $[Ca^{2+}]_i$ level in cells expressing either OAMB or Pa $oa_1$ in response to test chemicals is remarkably high. FIGS. 14A-14F, depict the effect of cinnamic alcohol (FIGS. 14A and 14B), eugenol (FIGS. 14C and 14D), and t-anethole (FIGS. 14E and 14F) on intracellular calcium $[Ca^{2+}]_i$ levels in HEK-293 cells either transfected with Pa $oa_1$ or OAMB. HEK-293 cells are incubated for 30 s before the addition of 25 μM tested agents. The arrow in the figures indicates addition of tested agents. The fluorescence ratio determined from excitation with 340 nm and 380 nm is plotted to indicate transient increase in $[Ca^{2+}]_i$ levels.

Generally, changes in $[Ca^{2+}]_i$ in cells expressing OAMB is more pronounced than changes in cells expressing Pa $oa_1$. Based on increased $[Ca^{2+}]_i$ level in cells expressing OAMB, cinnamic alcohol is the most potent agent tested in this example, followed by eugenol and trans-anethole. In cells expressing Pa $oa_1$, eugenol is the most potent agent tested in this example, followed by cinnamic alcohol then trans-anethole. The data suggest that elevation pattern of $[Ca^{2+}]_i$ levels is chemical-dependent. While application of octopamine induces an immediate but transient peak (~20 sec) in $[Ca^{2+}]_i$ level, as shown in FIG. 9, the peaked $[Ca^{2+}]_i$ level is slower in onset and has a longer recovery time (more than 3 min) in response to treatment with tested plant essential oils.

In cells expressing OAMB, the increase in $[Ca^{2+}]_i$ level in response to cinnamic alcohol is slower than the other two chemicals. In Pa $oa_1$-expressing cells, the increase in $[Ca^{2+}]_i$ in response to trans-anethole is slower than eugenol and cinnamic alcohol. Thus, the efficacy of coupling of both cloned octopamine receptors to different second messenger signaling varies with the chemical used.

D. Summary of the Effects of Treatment with Certain Plant Essential Oils

The present example studies the molecular interaction of plant essential oils with octopamine receptors from different insect species. Based on the characteristic features of octopamine receptors from American cockroach and fruit fly, the example characterizes certain molecular basis for insect species differences in response to plant essential oils. Although trans-anethole does not have a significant effect on binding to OAMB while eugenol and cinnamic alcohol do (FIG. 12), only trans-anethole increases cAMP level (FIG. 13) and $[Ca^{2+}]_i$ (FIGS. 14A-14F) through OAMB. These findings suggest that, in the case of trans-anethole, ionic interaction between the tested agent and the receptor is not critical for the activation of signaling down stream to OAMB.

On the other hand, while both eugenol and cinnamic alcohol decrease the binding activity to Pa $oa_1$ (FIG. 12), only eugenol decreases cAMP levelS through this receptor (FIG. 13). However, these two chemicals increase $[Ca^{2+}]_i$ through Pa $oa_1$ and OAMB (FIGS. 14A-14F). The data demonstrates that activation of Pa $oa_1$ by trans-anethole and cinnamic alcohol is not primarily coupled to cyclic nucleotide system. It appears that it is coupled to IP3-system, which activates the release of $Ca^{2+}$ ions from internal stores. Activation of Pa $oa_1$ by eugenol is found to be coupled to both adenylate cyclase/cAMP and IP3/$Ca^{2+}$ signaling cascades. Therefore, the current changes in cellular responses suggest that tested plant essential oils differing by only a single hydroxyl group or methoxy group in their chemical structure are capable of differentially coupling each octopamine receptor to different second messenger systems. The data also suggest that, activation of single GPCR such as Pa $oa_1$ or OAMB, may potentially couple to multiple second messenger systems. Thus, a single receptor may have a different pharmacological profile depending on which second messenger system is activated. The variability of the transmembrane regions and N-termini of Pa $oa_1$ and OAMB might determine the selectivity of tested monoterpenoids. In addition, conservation of certain transmembrane motifs and the variability of the intracellular loops might enable Pa $oa_1$ and OAMB to discriminate among the various G-protein subtypes upon treatment with tested monoterpenoids.

Protein alignment indicate that the regions of lowest similarity among these two proteins are in the amino terminus extending into TM1, extracellular loop2 between TM4 and TM5, intracellular loop between TM5 and TM6 and the carboxy termini following TM7 (FIG. 2). On the other hand, protein alignment indicates sequence conservation between Pa $oa_1$ and OAMB is greatest within the transmembrane domains (TMs).

EXAMPLE 6

Toxicity Testing Against Certain Insect Species

Toxicity bioassay against the wild type *Drosophila melanogaster* fly and American cockroach is performed to address insect species specificity in response to certain plant essential oils and to determine whether the cellular changes in Pa $oa_1$ and OAMB cell models in response to treatment with tested essential oils correlate with their insecticidal activity.

*Drosophila melanogaster* wild type strain is purchased from Carolina Biological Supply Company (Burlington, NC). Flies carrying the inactive (iav) mutation that exhibit low locomotor activity and poor mating success, both of which are associated with a deficiency in octopamine synthesis are obtained from Bloomington *Drosophila* Stock Center (flybase ID FBa10005570, stock# BL-6029 iav).

Plant essential oils, including: p-cymene [methyl(1-methylethyl)benzene], eugenol [2-methoxy-4-(2-propenyl)phenol], trans-anethole [1-methoxy-4-(1-propenyl)benzene], cinnamic alcohol [3-phenyl-2-propen-1-ol], α-terpineol [p-menth-1-en-8-ol], methyl salicylate [2-hydroxybenzoic acid methyl ester], 2-phenylethyl propionate, and geraniol [3,7-dimethyl-2,6-octadien-1-ol], are obtained from City Chemical (West Haven, Conn.) and tested for insect control activity. The chemical structures of these compounds are set forth in FIG. 11.

Acetonic solutions of plant essential oils are prepared and different concentrations of each, that give from 10%-100% mortality, are applied by topical application. Controls are treated with the same volume (0.5 µl/insect) of acetone. Replicates, with 5 insects per replicate, are used for each concentration. The mortality is calculated 24 hours after treatment. Data are subjected to probit analysis to determine $LD_{50}$ value for each compound. See Finney, 1971, Probit Analysis $3^{rd}$ Ed., Cambridge University Press, London, pg. 333.

To determine whether the octopamine/octopamine receptor (OA/OAR) system is involved in the toxicity of tested plant essential oils, octopamine synthesis mutant (iav) Drosophila melanogaster strain is topically treated with a dose equivalent to the determined $LD_{50}$ for wild type strain. For this study, the $LD_{50}$ values of eight monoterpenoid plant essential oils (p-cymene, eugenol, trans-anethole, cinnamic alcohol, α-terpineol, methyl salicylate, phenylethyl propionate, and geraniol) are determined against wild type as described above and being used to treat the octopamine mutant (iav) fruit fly. Controls are treated with the same volume (0.5 µl/fly) of acetone. The mortality is calculated 24 hour after treatment. Multiple replicates and 5 flies per replicate are used for the bioassay of each chemical. Data are subjected to probit analysis to determine $LD_{50}$ value for each chemical. See Finney, 1971.

To determine insect species differences in response to plant essential oil monoterpenoids, the toxicity of certain monoterpenoids is determined against fruit fly and American cockroach. Based on the calculated $LD_{50}$ values, shown in Table C, cinnamic alcohol is the most toxic chemical tested in the example ($LD_{50}$=1.65 µg/fly) against wild type fruit fly strain, followed by eugenol ($LD_{50}$=1.90 µg/fly), and trans-anethole ($LD_{50}$=6.00 µg/fly). Eugenol is about 2-fold and about 27-fold more toxic against American cockroach than cinnamic alcohol and trans-anethole, respectively.

TABLE C

| Plant essential oil | $LD_{50}$, µg/insect | |
|---|---|---|
| | D. melanogaster | P. Americana |
| Cinnamic alcohol | 1.65 | 98 |
| Eugenol | 1.90 | 47 |
| Trans-anethole | 6.00 | 1300 |

To determine whether the OA/OAR system mediates the toxicity of certain plant essential oil monoterpenoids, fruit flies carrying the iav mutations, which are highly susceptible to the octopamine analogue p-cresol, are used in parallel with wild type fruit fly strain in the toxicity 5 bioassay test. The toxicity of cinnamic alcohol, eugenol, trans-anethole and 2-phenyethyl propionate is remarkably increased when they are topically applied to the iav strain, as shown in Table D.

TABLE D

| Chemical name | Wild/type $LD_{50}$ values (µg/fly) | % Mortality at $LD_{50}$ of wild/type Drosophila melanogaster strain | |
|---|---|---|---|
| | | Wild/type | iav |
| cinnamic alcohol | 1.65 | 30.0% | 80.0% |
| eugenol | 1.90 | 53.3% | 80.0% |

TABLE D-continued

| Chemical name | Wild/type $LD_{50}$ values (µg/fly) | % Mortality at $LD_{50}$ of wild/type Drosophila melanogaster strain | |
|---|---|---|---|
| | | Wild/type | iav |
| trans-anethole | 6.00 | 40.0% | 100.0% |
| methyl salicylate | 7.50 | 40.0% | 46.6% |
| geraniol | 10.50 | 60.0% | 60.0% |
| α-terpineol | 13.00 | 46.6% | 60.0% |
| 2-phenylethyl propionate | 14.50 | 53.3% | 80.0% |
| p-cymene | 25.00 | 40.0% | 40.0% |

However, mutation of the octopamine synthesis does not affect the toxicity of p-cymene, methyl salicylate, and geraniol. Therefore, the current data suggests a correlation between agents inducing cellular changes in clonal cells expressing octopamine receptors and their insecticidal activity. The data also suggests that the insecticidal activity of cinnamic alcohol, eugenol, trans-anethole and 2-phenyethyl propionate is mediated through the octopamine/octopamine receptor system. From these data it can be concluded that the increase in the insecticidal activity of these chemicals results from the deficiency of octopamine synthesis in iav mutants because low octopamine levels may be unable to compete against the toxic effect of these chemicals.

As mentioned above, the toxicity data demonstrates significant differences between the toxicity of the tested chemicals against each insect (Table C). The toxicity data also demonstrates differences between the two insects in response to each chemical. The toxicity data against wild type and octopamine mutant (iav) fruit fly suggests that the toxicity of cinnamic alcohol, eugenol and trans-anethol is mediated through octopamine/octopamine receptors system. Among certain other plant essential oils tested against both strains of fruit fly only the toxicity of 2-phenylethyl propionate is mediated through octopamine receptors. Collectively the data suggest a correlation between cellular changes and toxicity of certain plant essential oils.

Figure 11:
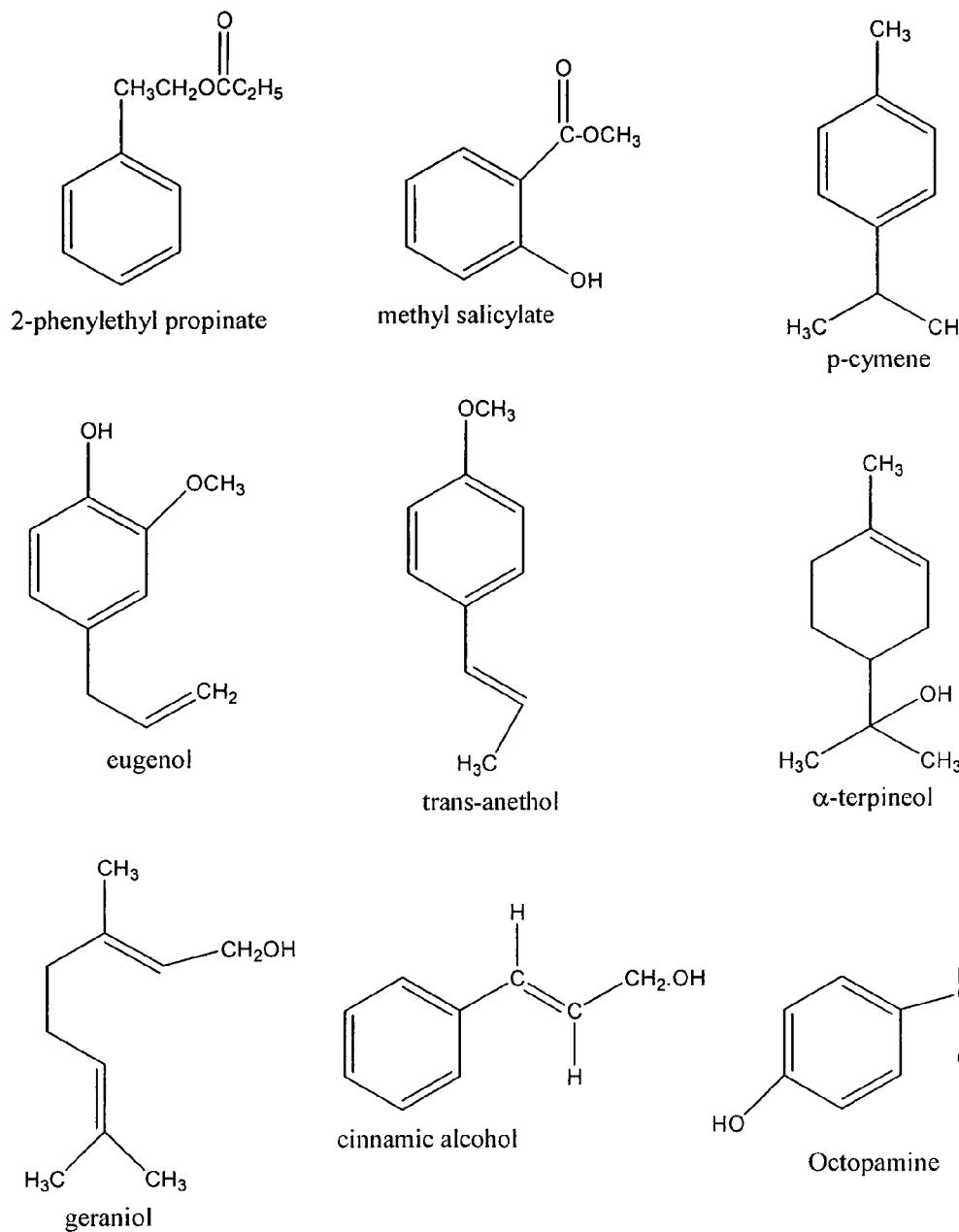
FIG. 11 is a depiction of the chemical structures of p-cymene [methyl(1-methylethyl)benzene], eugenol [2-methoxy-4-(2-propenyl)phenol], trans-anethole [1-methoxy-4-(1-propenyl)benzene], cinnamic alcohol [3-phenyl-2-propen-1-ol], α-terpineol [p-menth-1-en-8-ol], methyl salicylate [2-hydroxybenzoic acid methyl ester], 2-phenylethyl propionate, and geraniol [3,7-dimethyl-2,6-octadien-1-ol]

In the present example, chemical-structure relationships of plant essential oil monoterpenoids against wild type fruit fly suggest certain structural features required for chemical-receptor interaction. Among these features are the presence and location of a hydroxyl group, and a spacing group such as methoxy group. The rank order of toxicity demonstrates that cyclic alcohols and phenolic compounds are more toxic than other monoterpenoids such as acyclic alcohols and esters. The efficacy of each compound is found to be determined by the presence and location of the spacing group on the benzene ring. For example, although the phenolic derivative, eugenol, and propenyl benzene, trans-anethol, contain the same spacing group (—$OCH_3$) on position 2 and 1, respectively, eugenol is 3-fold more toxic against wild type flies than trans-anethole (FIG. 11 and Table D).

In summary, the similarities and differences between both Pa $oa_1$ and OAMB sequences are determining features in the toxicity differences of certain plant essential oil monoterpenoids. Additionally, it appears that the octopamine receptor mediates the insecticidal properties of cinnamic alcohol, eugenol, trans-anethole and 2-phenylethyl propionate and, in part, the toxicity of α-terpineol against Drosophila melanogaster fly. Furthermore, it appears that the presence of an electronegative group such as hydroxyl group, and different spacing groups, may be required for the insecticidal activity of plant essential oils through octopamine receptor.

It will be apparent to those skilled in the art that various modifications and variations can be made in the present invention without departing from the scope or spirit of the invention. It is intended that the Specification and Example be considered as exemplary only, and not intended to limit the scope and spirit of the invention. The references and publications cited herein are incorporated herein by this reference.

Unless otherwise indicated, all numbers expressing quantities of ingredients, properties such as reaction conditions, and so forth used in the Specification, Examples, and claims are to be understood as being modified in all instances by the term "about." Accordingly, unless indicated to the contrary, the numerical parameters set forth in the Specification, Example, and claims are approximations that may vary depending upon the desired properties sought to be determined by the present invention.

What is claimed is:

1. A method of screening compounds and/or compositions for potential insect control activity, comprising:
providing cells expressing an octopamine receptor and cells expressing a tyramine receptor;
adding said compounds and/or compositions to the cells thereb causing an effect through at least the tyramine receptor;
measuring the effects of the compounds and/or compositions, wherein measurable effects comprise a change in a level of cAMP and/or $Ca^{2+}$ within the cells, and wherein the effects are indicative of potential insect control activity. classifying the selected compounds and/or compositions as having potential insect control activity.

2. The method of claim 1, wherein the step of measuring the effects of the compounds and/or compositions includes measuring the binding affinity of said compounds and/or compositions to at least one of the said receptors.

3. The method of claim 2, additionally comprising selecting compounds and/or compositions having an affinity for at least one of the said receptors.

4. The method of claim 1, wherein the step of measuring the effects of the compounds and/or compositions includes: extracting intracellular cAMP and/or $Ca^{2+}$ from the cells; determining the intracellular cAMP and/or $Ca^{2+}$ levels; and comparing the intracellular cAMP and/or $Ca^{2+}$ levels in cells treated with said compounds and/or compositions to the intracellular cAMP and/or $Ca^{2+}$ levels in untreated cells.

5. The method of claim 4, additionally comprising selecting compounds and/or compositions, the treatment with which causes a change in intracellular cAMP and/or $Ca^{2+}$ levels.

6. A method of screening compounds and/or compositions for potential insect control activity, comprising:
providing first cells expressing a first octopamine receptor and cells expressing a tyramine receptor;
providing second cells expressing a second octopamine receptor;
adding said compounds and/or compositions to the first and the second cells thereby causing an effect through at least the tyramine receptor;
measuring the effects of the compounds and/or compositions, wherein measurable effects comprise a change in a level of cAMP and/or Ca$^{2+}$ within the cells, and wherein the effects are indicative of potential insect control activity. classifying the selected compounds and/or compositions as having potential insect control activity.

7. The method of claim 6, wherein the step of measuring the effects of the compounds and/or compositions includes measuring the binding affinity of said compounds and/or compositions to at least one of the said receptors.

8. The method of claim 7, and additionally comprising selecting compounds and/or compositions having a desired relative affinity for one of the said receptors.

9. The method of claim 6, wherein the step of measuring the effects of the compounds and/or compositions includes: extracting intracellular cAMP and/or Ca$^{2+}$ from the first and the second cells; determining the intracellular cAMP and/or Ca$^{2+}$ levels; and comparing the change in intracellular cAMP and/or Ca$^{2+}$ levels in the first cells and the second cells.

10. The method of claim 9, and additionally comprising selecting compounds and/or compositions, the treatment with which causes a desired relative change in intracellular cAMP and/or Ca$^{2+}$ levels in one of the cells.

11. The method of claim 9, wherein one of the octopamine receptors has an amino acid sequence of SEQ ID NO:3.

12. A method of testing the effects of compounds and/or compositions on cells, said method comprising:
    providing first cells expressing a first octopamine receptor cloned from a first insect species-of-interest and a tyramine receptor;
    providing second cells expressing a second octopamine receptor cloned from a second insect species-of-interest;
    adding said compounds and/or compositions to the first and the second cells thereby causing an effect through at least the tyramine receptor;
    measuring the effects of the compounds and/or compositions, wherein measurable effects comprise a change in a level of cAMP and/or Ca$^{2+}$ within the cells, and wherein the effects are indicative of potential insect control activity
    classifying the selected compound and/or compositions as having potential insect control activity.

13. The method of claim 1, wherein the octopamine receptor has an amino acid sequence of SEQ ID NO: 3.

14. The method of claim 1, wherein the octopamine

15. The method of claim 14, wherein the octopamine receptor is an octopamine receptor of an insect species.

16. The method of claim 6, wherein the first octopamine receptor is cloned from a first invertebrate, and the second octopamine receptor is cloned from a second invertebrate.

17. The method of claim 16, wherein the first octopamine receptor is cloned from a first insect species, and the second octopamine receptor is cloned from a second insect species.

18. The method of claim 2, additionally comprising excluding compounds and/or compositions having an affinity for the at least one receptor.

* * * * *

UNITED STATES PATENT AND TRADEMARK OFFICE
CERTIFICATE OF CORRECTION

PATENT NO.       : 7,622,269 B2                                              Page 1 of 1
APPLICATION NO.  : 11/086615
DATED            : November 24, 2009
INVENTOR(S)      : Essam Enan It is certified that error appears in the above-identified patent and that said Letters Patent is hereby corrected as shown below:

Item (73), Assignee on Cover Page; delete "Tyratech, Inc." and insert --TyraTech, Inc.--.

Column 12, line 54; delete "measurements A" and insert --measurements. A--.

Column 12, line 56-57; delete "col-lection Octopamine" and insert --col-lection. Octopamine--.

Column 13, line 7-8; delete "nM Tyramine" and insert --nM. Tyramine--.

Column 13, line 9; delete "tested These" and insert --tested. These--.

Column 17, line 50; delete "toxicity 5 bioassay" and insert --toxicity bioassay--.

Column 34, line 15; delete "octopamine" and insert --octopamine receptor is an octopamine receptor of an invertebrate.--.

Signed and Sealed this

Twenty-third Day of February, 2010

David J. Kappos
*Director of the United States Patent and Trademark Office*

UNITED STATES PATENT AND TRADEMARK OFFICE
CERTIFICATE OF CORRECTION

PATENT NO.       : 7,622,269 B2                                     Page 1 of 1
APPLICATION NO.  : 11/086615
DATED            : November 24, 2009
INVENTOR(S)      : Essam Enan It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 851 days.

Signed and Sealed this

Twenty-sixth Day of October, 2010

David J. Kappos
*Director of the United States Patent and Trademark Office*